United States Patent
Ullrich, Jr. et al.

(10) Patent No.: US 9,327,051 B2
(45) Date of Patent: *May 3, 2016

(54) IMPLANTS WITH INTEGRATION SURFACES HAVING REGULAR REPEATING SURFACE PATTERNS

(71) Applicant: Titan Spine, LLC, Mequon, WI (US)

(72) Inventors: Peter F. Ullrich, Jr., Neenah, WI (US); Chad J. Patterson, Port Washington, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/293,291

(22) Filed: Jun. 2, 2014

(65) Prior Publication Data

US 2014/0277512 A1 Sep. 18, 2014

Related U.S. Application Data

(63) Continuation of application No. 13/607,890, filed on Sep. 10, 2012, now Pat. No. 8,758,443, which is a continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)
*A61L 27/06* (2006.01)
(Continued)

(52) U.S. Cl.
CPC ............ *A61L 27/06* (2013.01); *A61F 2/3094* (2013.01); *A61F 2/4455* (2013.01);
(Continued)

(58) Field of Classification Search
CPC ........... A61F 2/4455; A61F 2002/4475; A61F 2002/30897; A61F 2002/30896; A61F 2002/30894; A61F 2002/30892; A61F 2002/30891; A61F 2002/30321; A61F 2002/30322; A61F 2002/0081

See application file for complete search history.

(56) References Cited

U.S. PATENT DOCUMENTS 4,314,876 A   2/1982   Kremer et al.
4,904,261 A   2/1990   Dove et al.
(Continued)

FOREIGN PATENT DOCUMENTS

EP   0599419   6/1994
EP   0916323   5/1999
(Continued)

OTHER PUBLICATIONS

Astra Tech Dental, "Nanolevel topographic modifications on the OsseoSpeed surface", http://shop.dentsplyimplants.us, Mar. 8, 2001.
(Continued)

*Primary Examiner* — Todd E Manahan
*Assistant Examiner* — Julianna N Harvey
(74) *Attorney, Agent, or Firm* — Stradley Ronon Stevens & Young, LLP

(57) ABSTRACT

An interbody spinal implant, such as a solid-body or composite implant. The implant has at least one integration surface with a roughened surface topography including a repeating pattern, without sharp teeth that risk damage to bone structures, adapted to grip bone through friction generated when the implant is placed between two vertebral endplates and to inhibit migration of the implant. The repeating pattern is formed of at least three at least partially overlapping repeating patterns. The repeating patterns may radiate at a fixed distance from at least one point and may include recesses having a slope of thirty degrees or less relative to the integration surface. Also disclosed are processes of fabricating the integration surfaces.

18 Claims, 25 Drawing Sheets

(a)

(b)

(51) Int. Cl.
*A61F 2/30* (2006.01)
*A61F 2/28* (2006.01)
*A61F 2/46* (2006.01)

(52) U.S. Cl.
CPC .......... *A61F 2/4465* (2013.01); *A61F 2/30965* (2013.01); *A61F 2/4611* (2013.01); *A61F 2002/2817* (2013.01); *A61F 2002/2835* (2013.01); *A61F 2002/30013* (2013.01); *A61F 2002/30014* (2013.01); *A61F 2002/3084* (2013.01); *A61F 2002/3093* (2013.01); *A61F 2002/3097* (2013.01); *A61F 2002/30133* (2013.01); *A61F 2002/30321* (2013.01); *A61F 2002/30405* (2013.01); *A61F 2002/30454* (2013.01); *A61F 2002/30604* (2013.01); *A61F 2002/30769* (2013.01); *A61F 2002/30772* (2013.01); *A61F 2002/30774* (2013.01); *A61F 2002/30779* (2013.01); *A61F 2002/30785* (2013.01); *A61F 2002/30787* (2013.01); *A61F 2002/30789* (2013.01); *A61F 2002/30797* (2013.01); *A61F 2002/30807* (2013.01); *A61F 2002/30836* (2013.01); *A61F 2002/30838* (2013.01); *A61F 2002/30843* (2013.01); *A61F 2002/30891* (2013.01); *A61F 2002/30892* (2013.01); *A61F 2002/30906* (2013.01); *A61F 2002/30925* (2013.01); *A61F 2002/30927* (2013.01); *A61F 2002/30973* (2013.01); *A61F 2002/30985* (2013.01); *A61F 2002/448* (2013.01); *A61F 2002/4475* (2013.01); *A61F 2002/4629* (2013.01); *A61F 2310/00017* (2013.01); *A61F 2310/00023* (2013.01); *A61F 2310/00047* (2013.01); *A61F 2310/00053* (2013.01); *A61F 2310/00131* (2013.01); *A61F 2310/00407* (2013.01); *Y10T 29/49* (2015.01)

(56) References Cited

U.S. PATENT DOCUMENTS

| | | |
|---|---|---|
| 5,015,247 A | 5/1991 | Michelson |
| 5,071,437 A * | 12/1991 | Steffee .................... A61F 2/442 606/247 |
| 5,258,098 A | 11/1993 | Wagner et al. |
| 5,306,309 A | 4/1994 | Wagner et al. |
| 5,425,772 A | 6/1995 | Brantigan |
| 5,443,514 A | 8/1995 | Steffee |
| 5,456,723 A | 10/1995 | Steinemann et al. |
| 5,507,815 A | 4/1996 | Wagner et al. |
| 5,571,188 A | 11/1996 | Ellingsen et al. |
| 5,603,338 A | 2/1997 | Beaty |
| 5,609,635 A | 3/1997 | Michelson |
| 5,702,449 A | 12/1997 | McKay |
| 5,755,798 A | 5/1998 | Papavero et al. |
| 5,766,252 A | 6/1998 | Henry et al. |
| 5,776,199 A | 7/1998 | Michelson |
| 5,860,973 A | 1/1999 | Michelson |
| 5,863,201 A | 1/1999 | Lazzara et al. |
| 5,865,845 A | 2/1999 | Thalgott |
| 5,876,453 A | 3/1999 | Beaty |
| 5,885,079 A | 3/1999 | Niznick |
| 5,888,224 A | 3/1999 | Beckers et al. |
| 5,922,029 A | 7/1999 | Wagner et al. |
| 5,968,098 A | 10/1999 | Winslow |
| 5,984,922 A | 11/1999 | McKay |
| 6,033,582 A | 3/2000 | Lee et al. |
| 6,039,762 A | 3/2000 | McKay |
| 6,059,829 A | 5/2000 | Schlapfer et al. |
| 6,080,158 A | 6/2000 | Lin |
| 6,086,613 A | 7/2000 | Camino et al. |
| 6,096,107 A | 8/2000 | Caracostas et al. |
| 6,123,705 A | 9/2000 | Michelson |
| 6,143,032 A | 11/2000 | Schafer et al. |
| 6,176,882 B1 | 1/2001 | Biedermann et al. |
| 6,183,255 B1 | 2/2001 | Oshida |
| 6,193,757 B1 | 2/2001 | Foley et al. |
| 6,193,762 B1 | 2/2001 | Wagner et al. |
| 6,241,770 B1 | 6/2001 | Michelson |
| 6,241,771 B1 | 6/2001 | Gresser et al. |
| 6,245,108 B1 | 6/2001 | Biscup |
| 6,296,664 B1 | 10/2001 | Middleton |
| 6,302,914 B1 | 10/2001 | Michelson |
| 6,342,074 B1 | 1/2002 | Simpson |
| 6,344,057 B1 | 2/2002 | Rabbe et al. |
| 6,350,283 B1 | 2/2002 | Michelson |
| 6,375,681 B1 | 4/2002 | Truscott |
| 6,387,130 B1 | 5/2002 | Stone et al. |
| 6,395,031 B1 | 5/2002 | Foley et al. |
| 6,423,095 B1 | 7/2002 | Van Hoeck et al. |
| 6,425,920 B1 * | 7/2002 | Hamada .................... 623/17.16 |
| 6,432,140 B1 | 8/2002 | Lin |
| 6,447,544 B1 | 9/2002 | Michelson |
| 6,458,159 B1 | 10/2002 | Thalgott |
| 6,478,823 B1 | 11/2002 | Michelson |
| 6,482,233 B1 | 11/2002 | Aebi et al. |
| 6,485,517 B1 | 11/2002 | Michelson |
| 6,491,723 B1 | 12/2002 | Beaty |
| 6,558,424 B2 | 5/2003 | Thalgott |
| 6,569,201 B2 | 5/2003 | Moumene et al. |
| 6,579,318 B2 | 6/2003 | Varga et al. |
| 6,592,624 B1 | 7/2003 | Fraser et al. |
| 6,599,322 B1 | 7/2003 | Amrich et al. |
| 6,610,089 B1 | 8/2003 | Liu et al. |
| 6,620,332 B2 | 9/2003 | Amrich |
| 6,635,086 B2 | 10/2003 | Lin |
| 6,652,765 B1 | 11/2003 | Beaty |
| 6,676,703 B2 | 1/2004 | Biscup |
| 6,702,855 B1 | 3/2004 | Steinemann et al. |
| 6,719,794 B2 | 4/2004 | Gerber et al. |
| 6,726,720 B2 | 4/2004 | Ross et al. |
| 6,730,127 B2 | 5/2004 | Michelson |
| 6,740,118 B2 | 5/2004 | Eisermann et al. |
| 6,743,231 B1 | 6/2004 | Gray et al. |
| 6,758,849 B1 | 7/2004 | Michelson |
| 6,833,006 B2 | 12/2004 | Foley et al. |
| 6,890,355 B2 | 5/2005 | Michelson |
| 6,902,581 B2 | 6/2005 | Walkenhorst et al. |
| 6,911,249 B2 | 6/2005 | Wagner et al. |
| 6,923,810 B1 | 8/2005 | Michelson |
| 6,974,480 B2 | 12/2005 | Messerli et al. |
| 6,981,975 B2 | 1/2006 | Michelson |
| 7,018,412 B2 | 3/2006 | Ferreira et al. |
| 7,018,418 B2 | 3/2006 | Amrich et al. |
| 7,041,137 B2 | 5/2006 | Fulton et al. |
| 7,044,972 B2 | 5/2006 | Mathys, Jr. et al. |
| 7,048,870 B1 | 5/2006 | Ellingsen et al. |
| 7,060,073 B2 | 6/2006 | Frey et al. |
| 7,066,961 B2 | 6/2006 | Michelson |
| 7,077,864 B2 | 7/2006 | Byrd, III et al. |
| 7,087,085 B2 | 8/2006 | Steinemann et al. |
| 7,112,224 B2 | 9/2006 | Liu et al. |
| 7,128,760 B2 | 10/2006 | Michelson |
| 7,137,997 B2 | 11/2006 | Paul |
| 7,144,428 B2 | 12/2006 | Anitua |
| 7,166,129 B2 | 1/2007 | Michelson |
| 7,169,183 B2 | 1/2007 | Liu et al. |
| D539,934 S | 4/2007 | Blain |
| 7,201,775 B2 | 4/2007 | Gorensek et al. |
| D541,940 S | 5/2007 | Blain |
| 7,220,280 B2 | 5/2007 | Kast et al. |
| 7,223,289 B2 | 5/2007 | Trieu et al. |
| 7,226,480 B2 | 6/2007 | Thalgott |
| 7,238,186 B2 | 7/2007 | Zdeblick et al. |
| 7,244,275 B2 | 7/2007 | Michelson |
| 7,250,060 B2 | 7/2007 | Trieu |
| 7,255,698 B2 | 8/2007 | Michelson |
| 7,288,093 B2 | 10/2007 | Michelson |
| 7,311,734 B2 | 12/2007 | Van Hoeck et al. |
| D564,095 S | 3/2008 | Blain |
| 7,347,873 B2 | 3/2008 | Paul et al. |
| D566,276 S | 4/2008 | Blain |

(56) References Cited

U.S. PATENT DOCUMENTS

| | | |
|---|---|---|
| 7,368,065 B2 | 5/2008 | Yang et al. |
| 7,410,501 B2 | 8/2008 | Michelson |
| 7,501,073 B2 | 3/2009 | Wen et al. |
| 7,503,933 B2 | 3/2009 | Michelson |
| 7,517,363 B2 | 4/2009 | Rogers et al. |
| D599,019 S | 8/2009 | Pimenta et al. |
| 7,569,074 B2 | 8/2009 | Eisermann et al. |
| 7,608,107 B2 | 10/2009 | Michelson |
| 7,615,078 B2 | 11/2009 | White et al. |
| 7,655,042 B2 | 2/2010 | Foley et al. |
| 7,662,186 B2 | 2/2010 | Bagga et al. |
| 7,662,190 B2 | 2/2010 | Steinemann et al. |
| 7,744,612 B2 | 6/2010 | Blain |
| 7,846,183 B2 | 12/2010 | Blain |
| 7,901,462 B2 | 3/2011 | Yang et al. |
| 7,998,172 B2 | 8/2011 | Blain |
| 8,062,304 B2 | 11/2011 | Blain et al. |
| 8,100,955 B2 | 1/2012 | Blain et al. |
| 8,142,355 B2 | 3/2012 | Blain et al. |
| 8,172,854 B2 | 5/2012 | Blain et al. |
| 8,262,737 B2 | 9/2012 | Bagga et al. |
| 2001/0014826 A1 | 8/2001 | Biedermann et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0049497 A1 | 4/2002 | Mason |
| 2002/0087212 A1 | 7/2002 | James et al. |
| 2002/0099443 A1 | 7/2002 | Messerli et al. |
| 2002/0128716 A1 | 9/2002 | Cohen et al. |
| 2002/0138142 A1 | 9/2002 | Castro et al. |
| 2002/0161443 A1 | 10/2002 | Michelson |
| 2002/0173854 A1 | 11/2002 | Amrich |
| 2002/0188294 A1 | 12/2002 | Couture et al. |
| 2003/0014116 A1 | 1/2003 | Ralph et al. |
| 2003/0083668 A1 | 5/2003 | Rogers et al. |
| 2003/0105527 A1* | 6/2003 | Bresina .............. A61B 17/1637 623/17.16 |
| 2003/0109928 A1 | 6/2003 | Pasquet et al. |
| 2003/0125739 A1 | 7/2003 | Bagga et al. |
| 2003/0153975 A1 | 8/2003 | Byrd, III et al. |
| 2003/0176925 A1 | 9/2003 | Paponneau |
| 2003/0181980 A1 | 9/2003 | Berry et al. |
| 2003/0181981 A1 | 9/2003 | Lemaire |
| 2003/0187506 A1 | 10/2003 | Ross et al. |
| 2003/0191531 A1 | 10/2003 | Berry et al. |
| 2004/0117020 A1 | 6/2004 | Frey et al. |
| 2004/0127993 A1 | 7/2004 | Kast et al. |
| 2004/0153154 A1 | 8/2004 | Dinkelacker |
| 2004/0153160 A1 | 8/2004 | Carrasco |
| 2004/0162316 A1 | 8/2004 | Howard, Jr. |
| 2004/0162616 A1 | 8/2004 | Simonton et al. |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0161120 A1* | 7/2005 | Inagaki ............... A61C 8/0012 148/220 |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0195209 A1 | 8/2008 | Garcia et al. |
| 2008/0221689 A1 | 9/2008 | Chaput et al. |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2008/0288076 A1* | 11/2008 | Soo et al. .................. 623/17.16 |
| 2009/0005784 A1 | 1/2009 | Blain et al. |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2011/0040301 A1 | 2/2011 | Blain et al. |
| 2011/0082503 A1 | 4/2011 | Blain |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wenzel |
| 2012/0149991 A1 | 6/2012 | Blain et al. |
| 2012/0158056 A1 | 6/2012 | Blain |
| 2012/0172991 A1 | 7/2012 | Bertele et al. |

FOREIGN PATENT DOCUMENTS

| | | |
|---|---|---|
| EP | 1449544 | 8/2004 |
| EP | 2 386 274 A1 | 11/2011 |
| EP | 2386274 | 11/2011 |
| JP | 08010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004041131 | 5/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |

(56) References Cited

FOREIGN PATENT DOCUMENTS

| WO | 2009029458 | 3/2009 |
| WO | 2009129262 | 10/2009 |
| WO | 2009140544 | 11/2009 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growith of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011.

Supplementary Partial European Search Report issued Aug. 19, 2011.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

* cited by examiner

IMPLANTS WITH INTEGRATION SURFACES HAVING REGULAR REPEATING SURFACE PATTERNS

CROSS REFERENCE TO RELATED APPLICATIONS

This application is a continuation of U.S. patent application Ser. No. 13/607,890, filed Sep. 10, 2012, which is a continuation-in-part of U.S. patent application Ser. No. 12/151,198, filed on May 5, 2008, and issued as U.S. Pat. No. 8,262,737, which is a continuation-in-part of U.S. patent application Ser. No. 11/123,359, filed on May 6, 2005, and issued as U.S. Pat. No. 7,662,186. The contents of all prior applications are incorporated by reference into this document, in their entirety and for all purposes.

TECHNICAL FIELD

The present invention relates generally to interbody spinal implants and processes of making such implants and, more particularly, to spinal implants having specially designed integration surfaces.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach, for example. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

There are a number of problems, however, with traditional spinal implants including, but not limited to, improper seating of the implant, implant subsidence (defined as sinking or settling) into the softer cancellous bone of the vertebral body, poor biomechanical integrity of the endplates, damaging critical bone structures during or after implantation, and the like. In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

In addition, a number of problems may occur with implants having teeth or sharp surface features. In particular, the teeth may cause severe damage to the vertebral endplates during and after insertion of the implant. For example, the teeth may scribe the surface of the vertebral endplates during insertion. The teeth or sharp features may cause the bone to dissolve and remodel under the load encountered after implantation. The points on the teeth may also have poor contact with the vertebral surface and may cause instability of the implant during and after implantation.

SUMMARY OF THE INVENTION

The present invention provides for interbody spinal implants having specially designed external surface features or integration surfaces. The integration surfaces of the implant may be provided with at least three partially overlapping repeating patterns, for example, to enhance friction, stabilize the implant during and after implantation, disperse the load applied across the implant, and prevent or minimize damage to the vertebral endplates.

Various implant body shapes are provided to allow for implantation through various access paths to the spine through a patient's body. The structures and surfaces are designed to work in concert to preserve endplate bone structures, provide for sufficient bioactivity in each respective location, and provide stability within the disc space and the graft containment axial column. In particular, the shapes and textures of the bioactive surfaces vary based on the implant insertion path, location within the disc space, and frictional characteristics of the surfaces.

In one embodiment, the present invention provides an interbody spinal implant comprising a body having a top surface, a bottom surface, opposing lateral sides, opposing anterior and posterior portions, a substantially hollow center, and a single vertical aperture defining at least one surface.

The implant can optionally include a composite implant having at least one of a first integration plate affixed to the top surface of the body and a second integration plate affixed to the bottom surface of the body, where the first integration plate and the second integration plate each have a top surface, a bottom surface, opposing lateral sides, opposing anterior and posterior portions, and a single vertical aperture defining at least one surface and extending from the top surface to the bottom surface and aligning with the single vertical aperture of the body.

The top and bottom surfaces of the implant in contact with the vertebrae (e.g., the outer surfaces) may define at least one integration surface having a roughened surface topography including a repeating pattern. The integration surfaces may have a fusion and biologically active surface geometry that frictionally engages preserved bone structures. In particular, the integration surfaces may have a roughened surface topography, without sharp teeth that risk damage to bone structures, adapted to grip bone through friction generated when the implant is placed between two vertebrae and to inhibit migration and expulsion of the implant.

The repeating pattern is formed of at least three at least partially overlapping repeating patterns comprising a first repeating pattern, a second repeating pattern, and a third repeating pattern. The second repeating pattern, the third repeating pattern, or both patterns may radiate at a fixed distance from at least one point defined by the first repeating pattern. The three repeating patterns may be formed from recesses each having a slope of 30° or less relative to the integration surface. For example, the first repeating pattern may be formed from recesses having a slope of 30° or less, the second repeating pattern may be formed from recesses having a slope of 25° or less, and the third repeating pattern may be formed from recesses having a slope of 20° or less relative to the integration surface. Preferably, the three repeating patterns have no undercuts or sharp points.

The three repeating patterns may include the first repeating pattern having a greatest depth, the second repeating pattern having an intermediate depth, and the third repeating pattern having a smallest depth. The three repeating patterns may also have a set spacing (e.g., the distance between the recesses) where the spacing S1 of the first repeating pattern is less than the spacing S3 of the third repeating pattern, which is less than the spacing S2 of the second repeating pattern.

Each of the patterns may include an array of dots, spheres, semi-spheres, cubes, polyhedral pyramids, or amorphous shapes of the same or varying diameters. Preferably, each of the three repeating patterns comprise features having diameters, depths, and spacings which are sequentially sized and positioned to preserve an amount of the features and patterns from the previous pattern.

The integration surface may include the top surface, the bottom surface, or both surfaces of the implant. In the case of no integration plates, this would include the top, bottom, or both surfaces of the body of the implant. In the case of one integration plate affixed to the top of the body of the implant, this would include the top of the integration plate, the bottom of the body, or both surfaces. In the case of one integration plate affixed to the bottom of the body of the implant, this would include the top of the body, the top of the integration plate (i.e., the outer surface of the integration plate at the bottom of the implant), or both surfaces. In the case of two integration plates sandwiched around the body of the implant, this would include the top of the first integration plate, the top of the second integration plate, or both surfaces (i.e., the outer surfaces of both integration plates at the top and bottom of the implant).

Other areas of the implant may include low friction surfaces (e.g., a soft tissue surface) and internal surfaces (e.g., graft retention surfaces). The soft tissue surfaces may be smooth, for example, to avoid unintentional laceration or abrasion of delicate soft tissues (e.g., blood vessels, nerves, and muscles) the implant contacts during insertion, after insertion, or both. The graft retention surfaces may be designed to promote retention of graft materials once placed inside the implant.

The implant body and/or the integration plate(s) may be fabricated from a metal. A preferred metal is titanium or a titanium alloy. The implant body may be fabricated from both a metal and a non-metallic material. In one embodiment, a composite implant may be formed with integration plates made of titanium combined with a body also made of titanium.

The present invention also encompasses a process of fabricating the surface features with a predetermined surface topography. The process may include cutting at least three distinct repeating patterns, which may at least partially overlap, designed to disperse the load applied across the implant, generate friction between the surface and the contacting bone, and stabilize the implant during and after implantation. For example, the process may include forming first-cut surface features having a spacing S1 and a greatest depth; forming second-cut surface features having a spacing S2 and an intermediate depth; and forming third-cut surface features having a spacing S3 and a smallest depth, where the spacing S1<spacing S3<spacing S2.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 16:
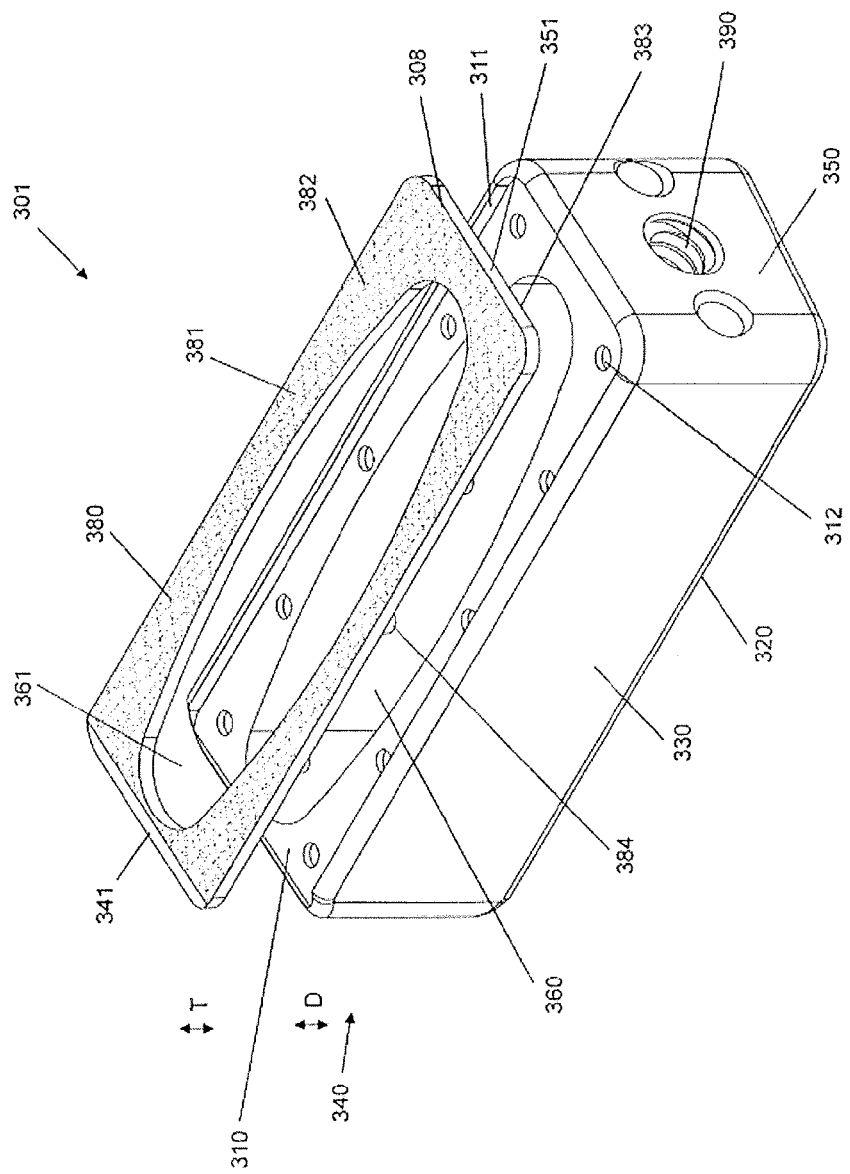
FIG. 16 shows an exploded view of a lateral lumbar implant with an integration plate.
Figure 17:
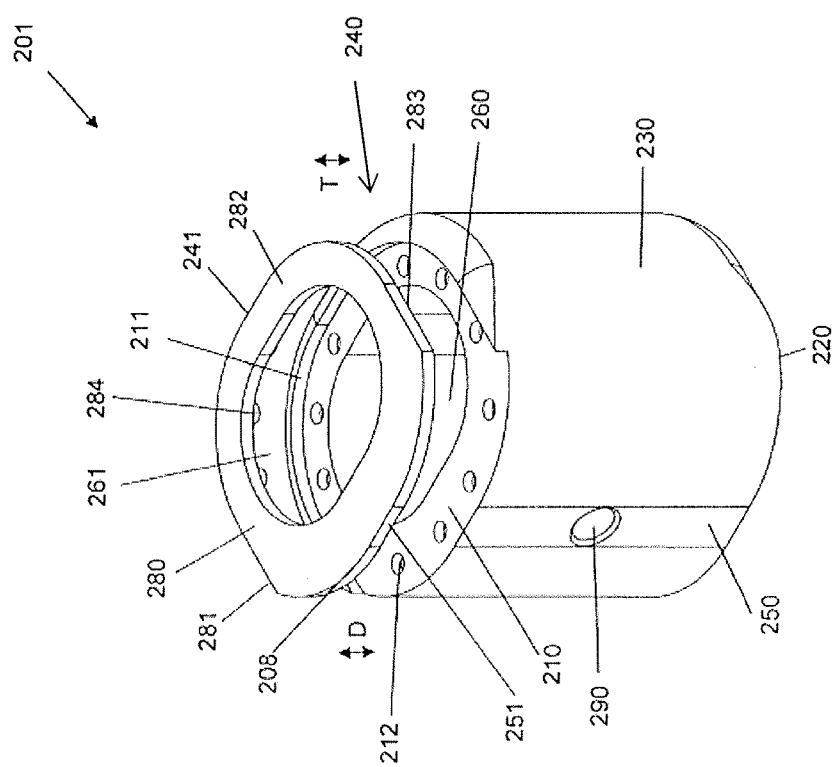
FIG. 17 shows an exploded view of a generally oval-shaped anterior cervical implant with an integration plate.

Certain embodiments of the present invention may be especially suited for placement between adjacent human vertebral bodies. The implants of the present invention may be used in procedures such as Anterior Lumbar Interbody Fusion (ALIF) (e.g., FIG. 4A), Posterior Lumbar Interbody Fusion (PLIF) (e.g., FIG. 15), Transforaminal Lumbar Interbody Fusion (TLIF) (e.g., FIG. 14), cervical fusion or Anterior Cervical implants (e.g., FIG. 17), and laterally placed lumbar implants (e.g., FIG. 16). Certain embodiments do not extend beyond the outer dimensions of the vertebral bodies.

The ability to achieve spinal fusion may be directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the present invention, allow for improved visualization of implant seating and fusion assessment. Interbody spinal implants, as now taught, may also facilitate osteointegration (e.g., formation of a direct structural and functional interface between the artificial implant and living bone) with the surrounding living bone. In addition, interbody spinal implants, according to certain aspects of the present invention, enhance friction, stabilize the implant during and after implantation, disperse the load applied across the implant, and prevent or minimize damage to the vertebral endplates during and after implantation.

It is generally believed that the surface of an implant determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the stimulation and proliferation of bone modeling and forming cells, such as osteoclasts and osteoblasts and like-functioning cells, upon the implant surface. Still further, it appears that these cells attach more readily to relatively rough surfaces rather than smooth surfaces. In this manner, a surface may be bioactive due to its ability to stimulate bio-chemical reaction, cellular attachment and osteointegration. The roughened surface topography of the integration plate(s) described in this document may better promote the osteointegration of certain embodiments of the present invention. The roughened surface topography of the integration plate(s) may also better grip the vertebral endplate surfaces, provide stability, and inhibit implant migration upon placement and seating as well as avoid or minimize damage to the vertebral endplate surfaces.

Implant Structure

Figure 4A:
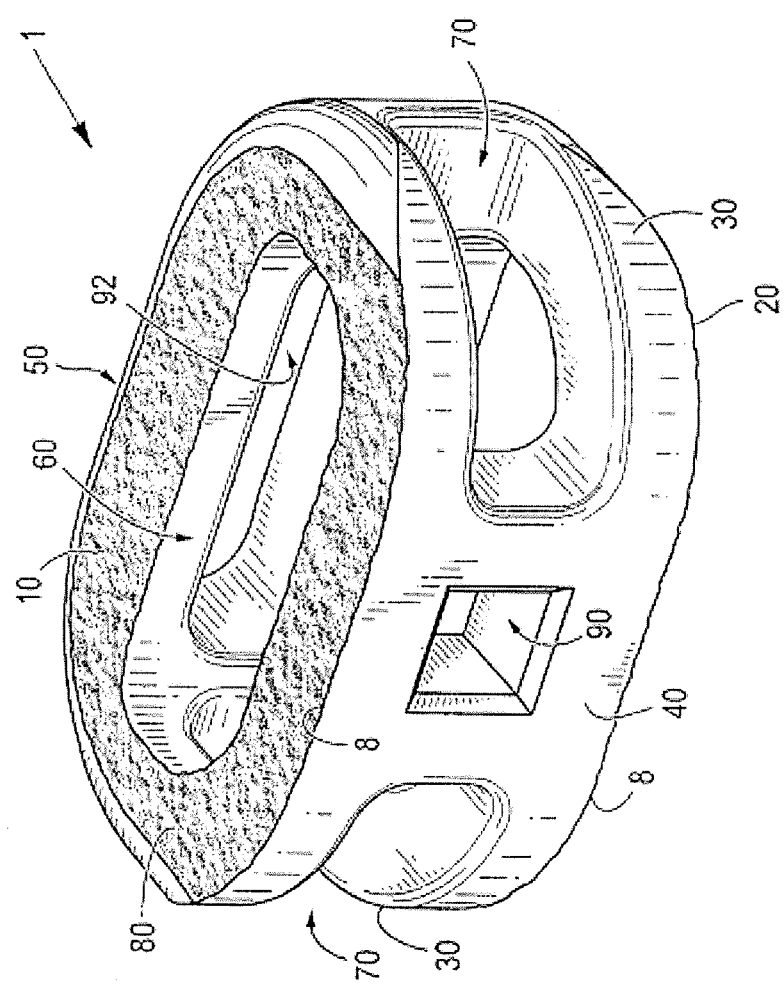
FIG. 4A shows a perspective view of an embodiment of the interbody spinal implant having a generally oval shape and roughened surface topography on the top surface.
Figure 4B:
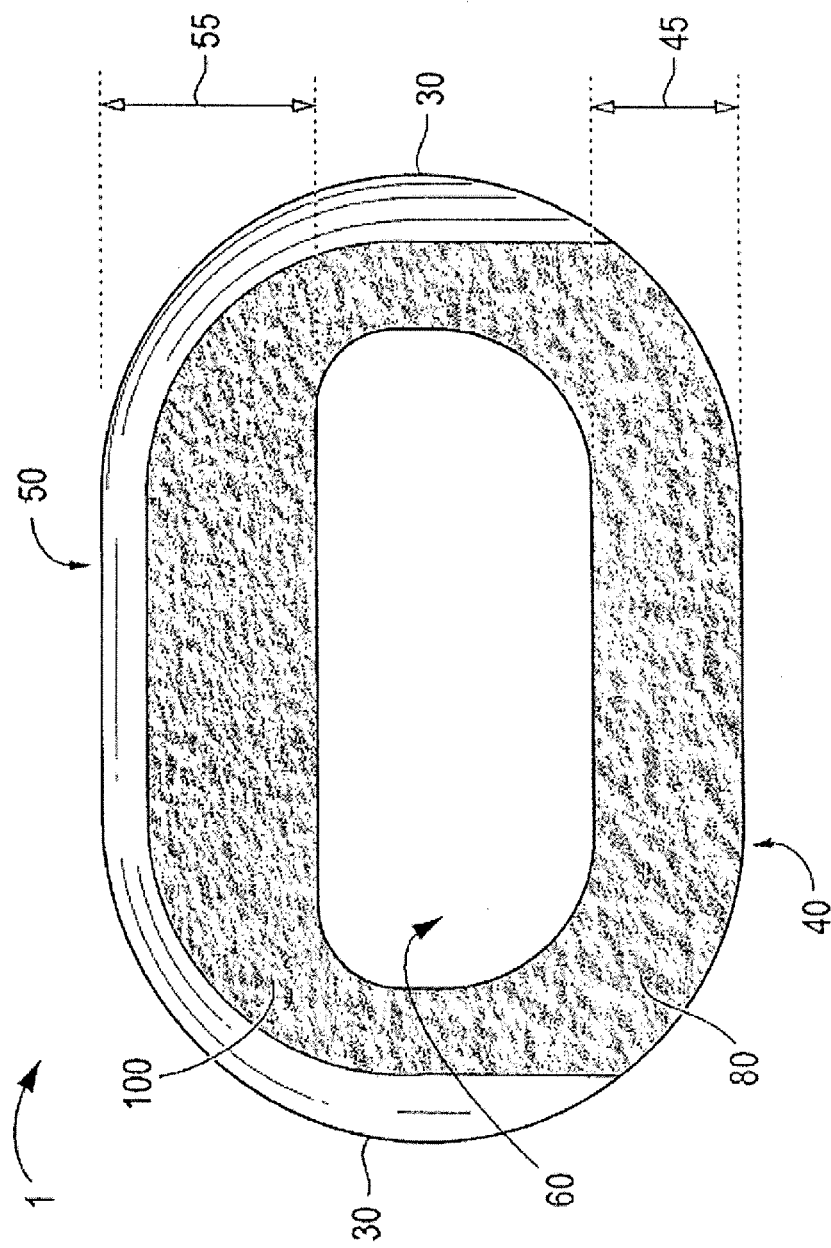
FIG. 4B shows a top view of the embodiment of the interbody spinal implant illustrated in FIG. 4A.

Referring now to the drawing, in which like reference numbers refer to like elements throughout the various figures that comprise the drawing, FIG. 4A shows a perspective view of a first embodiment of the interbody spinal implant 1 especially well adapted for use in an ALIF procedure. FIG. 4B shows a top view of the first embodiment. The interbody spinal implant 1 includes a body 2 having a top surface 10, a bottom surface 20, opposing lateral sides 30, and opposing anterior 40 and posterior 50 portions. The interbody spinal implant 1 may include implants made of a single piece of material or composite implants.

Interbody spinal implants 1 made of a single piece of material do not include integration plates 82. Thus, the integration surface may include the top surface 10 of the body 2 of the implant 1, the bottom surface 20 of the body 2 of the implant 1, or both surfaces. The integration surfaces may have a roughened surface topography 80 without sharp teeth that risk damage to bone structures. The implant 1 may be composed of a suitable biocompatible material. In an exemplary embodiment, implant 1 is formed of metal. The metal may be coated or not coated. Suitable metals, such as titanium, aluminum, vanadium, tantalum, stainless steel, and alloys of those metals, may be selected by one of ordinary skill in the art. In a preferred embodiment, however, the metal is at least one of titanium, aluminum, and vanadium, without any coatings. In a more preferred embodiment, the implant 1 is comprised of titanium or a titanium alloy. An oxide layer may naturally form on a titanium or titanium alloy. Titanium and its alloys are generally preferred for certain embodiments of the present invention due to their acceptable, and desirable, strength and biocompatibility. In this manner, certain embodiments of the present interbody spinal implant 1 may have improved structural integrity and may better resist fracture during implantation by impact.

Figure 12:
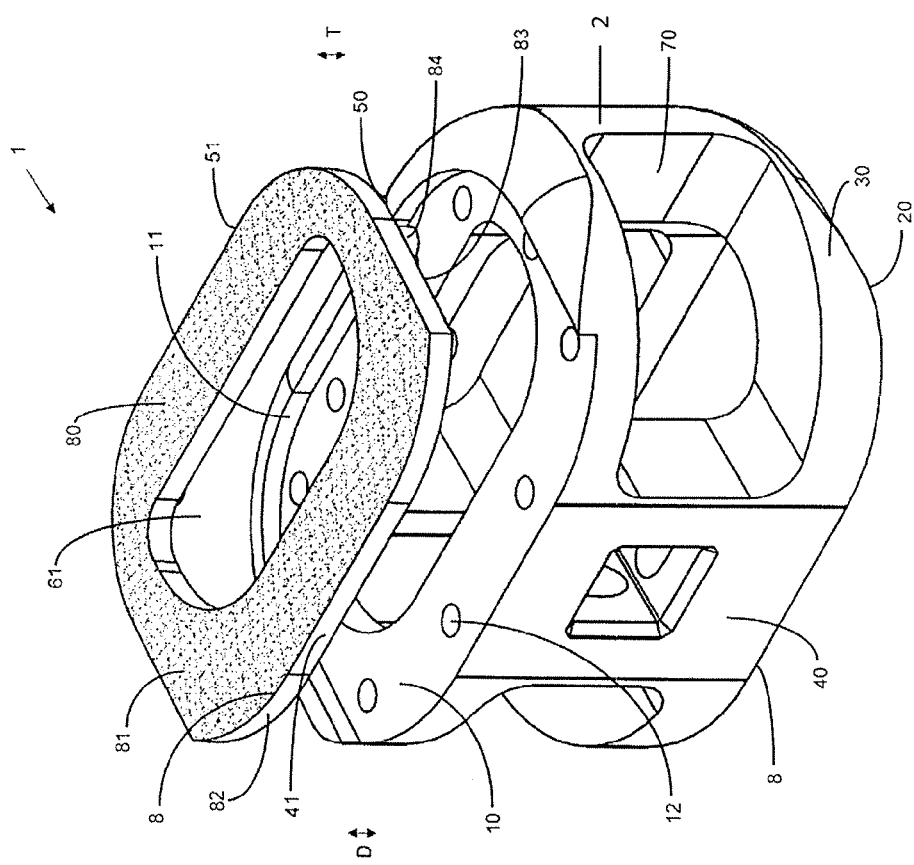
FIG. 12 shows an exploded view of a generally oval-shaped implant with an integration plate.
Figure 13:
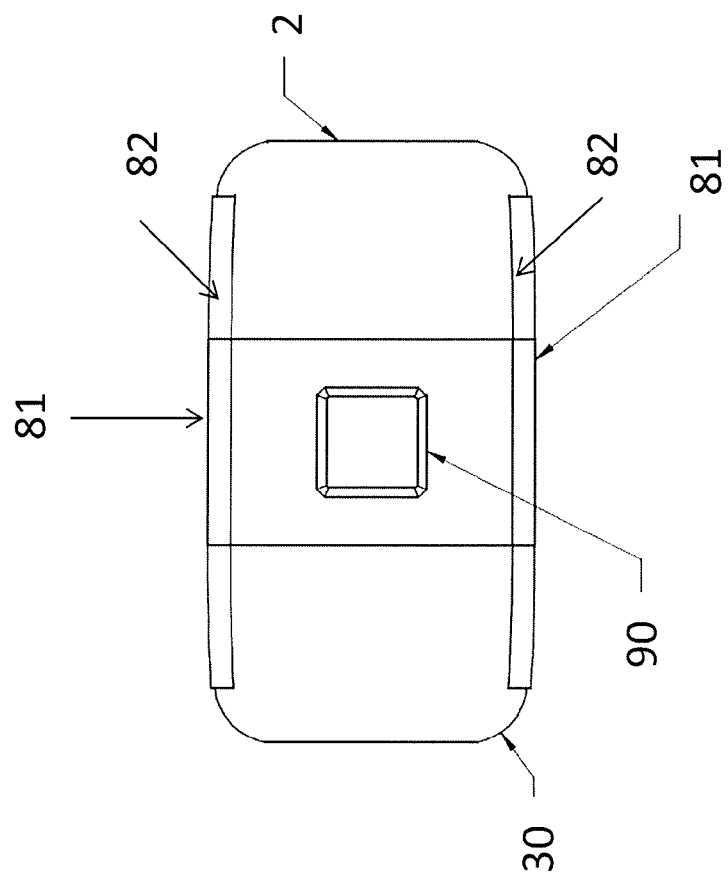
FIG. 13 shows an anterior view of an embodiment of the interbody spinal implant having two integration plates, which sandwich the body of the implant.

Composite implants 1 include at least a body 2 and one or two integration plates 82, which may be formed from the same or different materials. As depicted in FIG. 12, the implant 1 may include an optional first integration plate 82 affixed to the top surface 10 of the body 2 and an optional second integration plate 82 affixed to the bottom surface 20 of the body 2 (see FIG. 13). The optional first integration plate 82 and optional second integration plate 82 each have a top surface 81, a bottom surface 83, opposing lateral sides, an opposing anterior portion 41 and a posterior portion 51, and a single vertical aperture 61 extending from the top surface 81 to the bottom surface 83 and aligning with a single vertical aperture 60 of the body 2.

When present, the integration plate(s) 82 may comprise an integration surface (e.g., the top surface 81 of the first integration plate 82, the top surface 81 of the second integration plate 82, or both surfaces), which is adapted to grip bone through friction generated when the implant 1 is placed between two vertebrae and to inhibit migration of the implant 1 once implanted. The integration surfaces may also have a fusion stimulating and biologically active surface geometry. In other words, at least a portion of the top surface 81 of the first integration plate 82 (e.g., a first integration surface) and optionally a top surface 81 of the second integration plate 82 (e.g., a second integration surface) may have the roughened surface topography 80 without sharp teeth that risk damage to bone structures. The roughened surface topography 80 may include macro features of a regular repeating pattern, which may promote biological and chemical attachment or fusion with the bone structure.

The body 2 and at least one integration plate 82 are preferably compatibly shaped, such that the implant 1 having the body 2 and integration plate(s) 82 joined together may have a generally oval shape, a generally rectangular shape, a generally curved shape, or any other shape described or exemplified in this specification. Thus, for example, the body 2 and the integration plate(s) 82 may be generally oval-shaped in transverse cross-section. The body 2 and the integration plate(s) 82 may be generally rectangular-shaped in transverse cross-section. The body 2 and the integration plate(s) 82 may be generally curved-shaped in transverse cross-section.

The body 2 and integration plate(s) 82 of the implant 1 may be the same material or may be different. The body 2 and the integration plate(s) 82 may be composed of a suitable biocompatible material. In an exemplary embodiment, the body 2 and optional integration plate(s) 82 are formed of metal, which may be coated or not coated. Suitable metals, such as titanium, aluminum, vanadium, tantalum, stainless steel, and alloys of the metals, may be selected by one of ordinary skill in the art. In a preferred embodiment, however, the metal is at least one of titanium, aluminum, and vanadium, without any coatings. In a more preferred embodiment, the body 2 and optional integration plate(s) 82 are comprised of titanium or a titanium alloy. An oxide layer may naturally form on a titanium or titanium alloy.

Alternatively, the body 2 may be composed of a non-metal biocompatible material. In one embodiment, the body 2 of the implant 1 is formed of a plastic, polymeric, or composite material. For example, suitable polymers may comprise silicones, polyolefins, polyesters, polyethers, polystyrenes, polyurethanes, acrylates, and co-polymers and mixtures of the polymers. Certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. In another embodiment, the body 2 comprises polyetherether-ketone (PEEK), hedrocel, or ultra-high molecular weight polyethylene (UHMWPE). Hedrocel is a composite material composed of carbon and an inert metal, such as tantalum. UHMWPE, also known as high-modulus polyethylene (HMPE) or high-performance polyethylene (HPPE), is a subset of the thermoplastic polyethylene, with a high molecular weight, usually between 2 and 6 million.

Certain embodiments of the interbody spinal implant 1 are substantially hollow and have a generally oval-shaped transverse cross-sectional area. Substantially hollow, as used in this document, means at least about 33% of the interior volume of the interbody spinal implant 1 is vacant. Still further, the substantially hollow portion may be filled with graft materials, such as cancellous autograft bone, allograft bone, demineralized bone matrix (DBM), porous synthetic bone graft substitute, bone morphogenic protein (BMP), or combinations of those materials.

Integration Surface

The implant 1 may include an integration surface on at least a portion of the top surface, bottom surface, or both surfaces. As used in this document, the integration surface is the surface at least partially in contact with the vertebral endplate or bone structure. The composition of the endplate is a thin layer of notch-sensitive bone that is easily damaged by features (such as teeth) that protrude sharply from the surface of traditional implants.

Figure 1A:
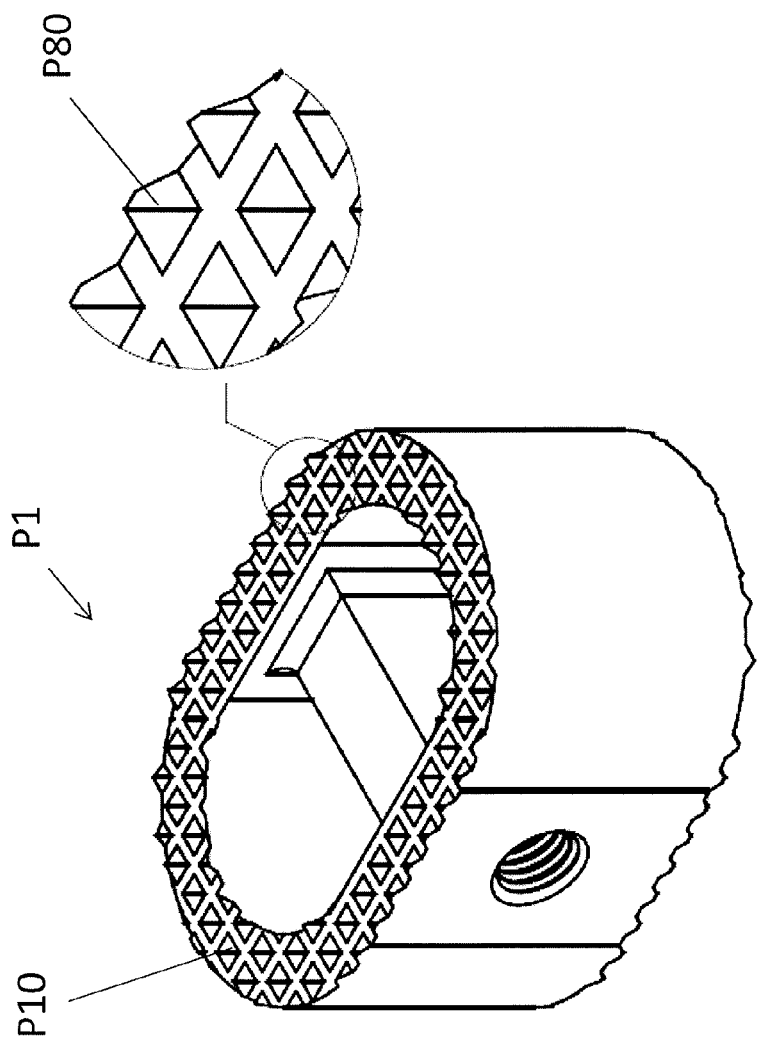
FIG. 1A shows a perspective view of an implant having teeth according to the prior art.
Figure 1B:
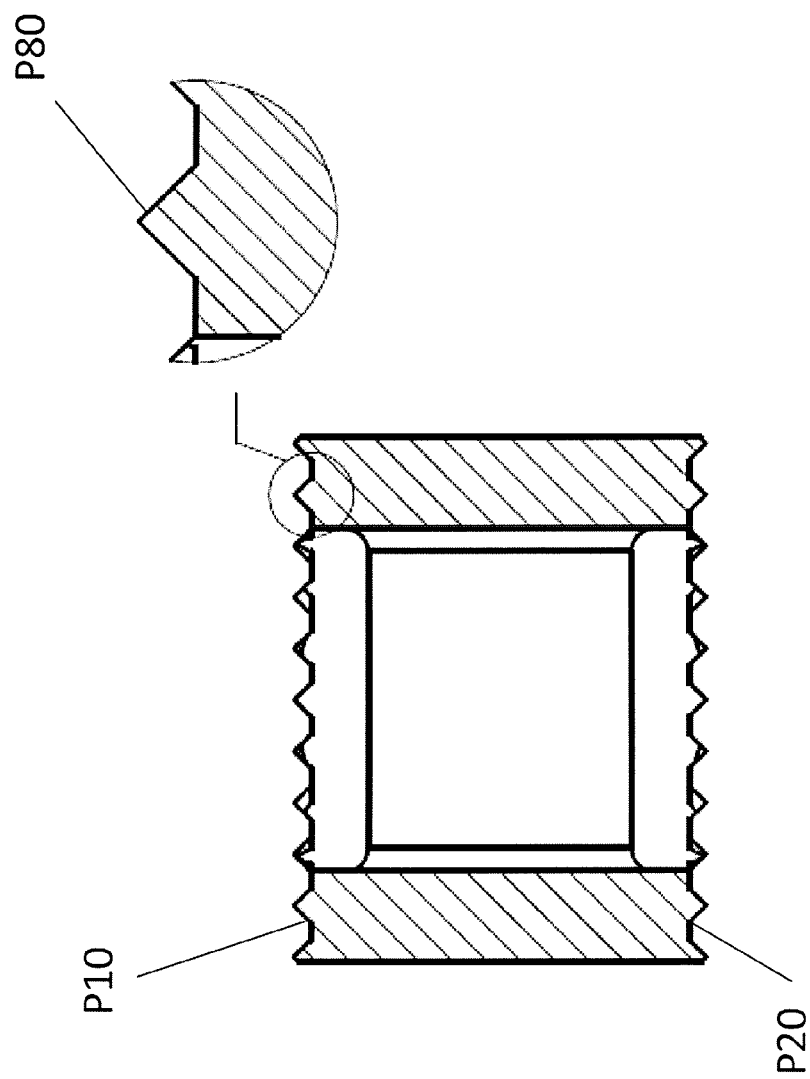
FIG. 1B shows a side view of the implant illustrated in FIG. 1.
Figure 2:
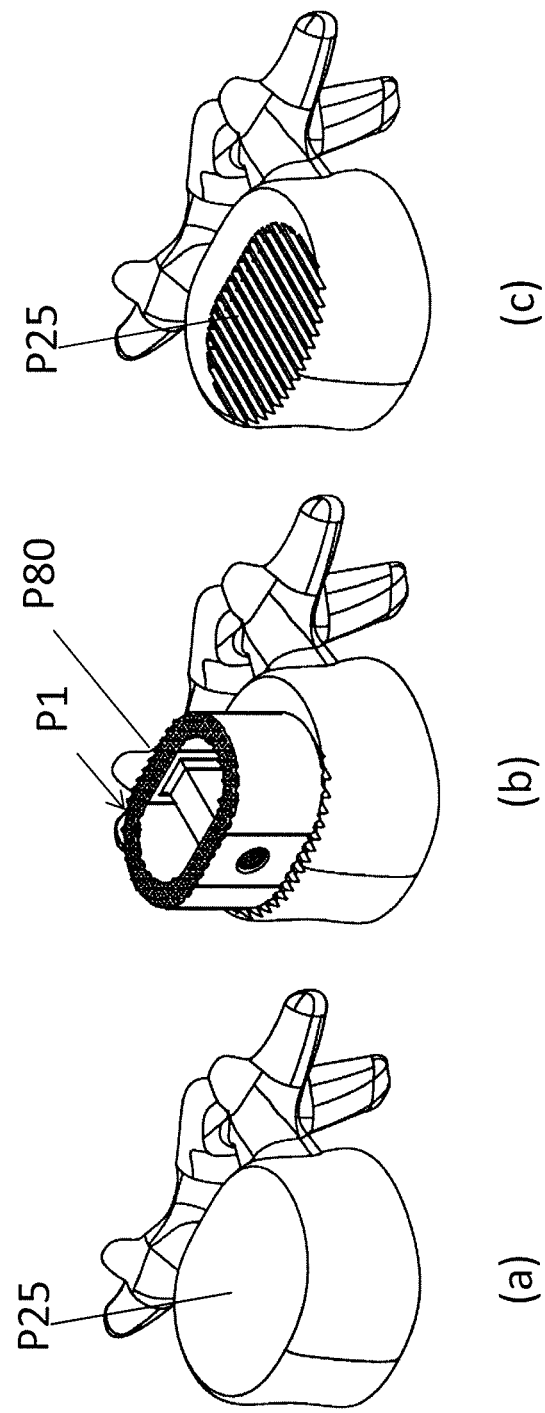
FIG. 2 shows the damage that may occur to the vertebrae using an implant according to the prior art where (a) is the endplate condition prior to implantation; (b) is the endplate condition when the implant is force fit into the joint space; and (c) is the resulting damage to the endplate due to the presence of teeth on the implant.
Figure 3:
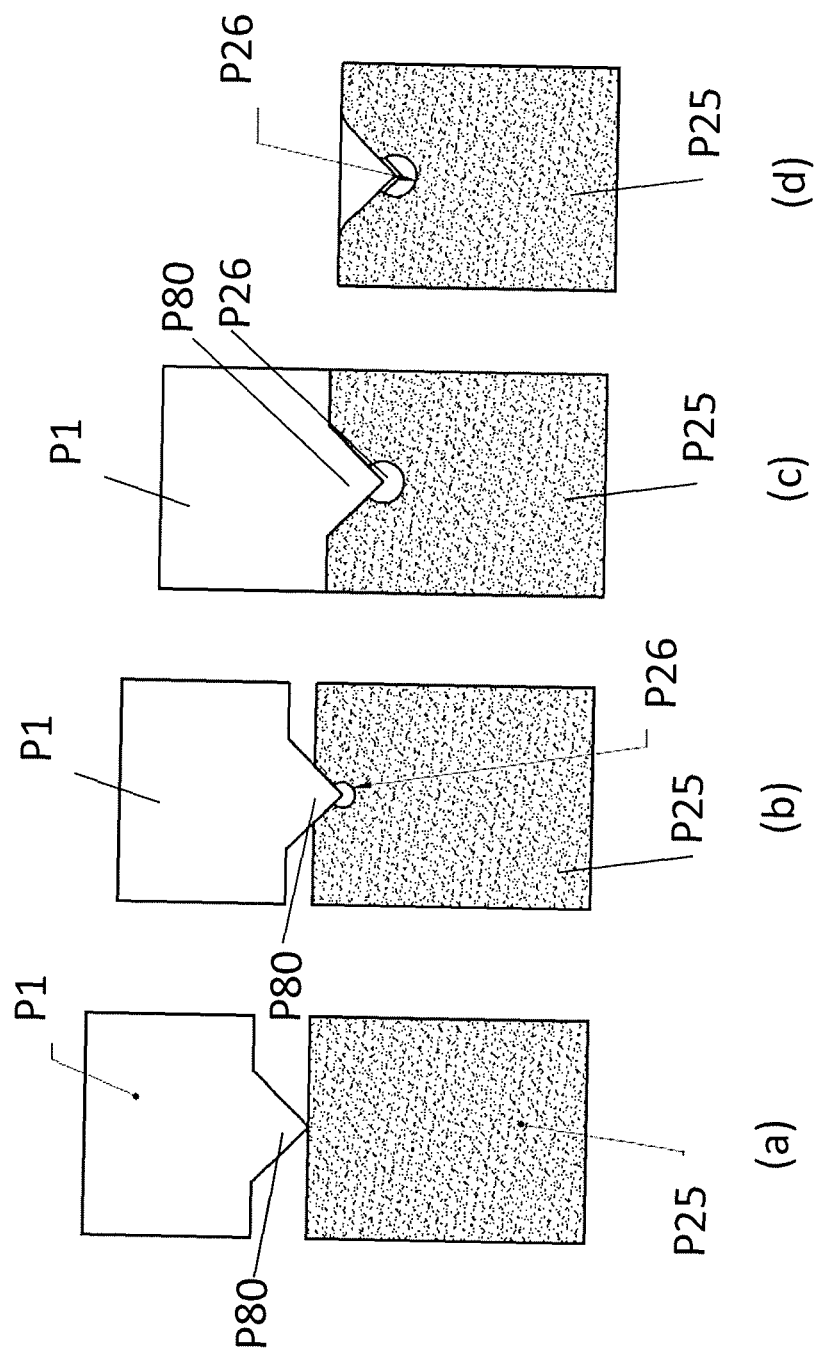
FIG. 3 shows the progression of bone remodeling under a focused load of sharp surface features using an implant having teeth according to the prior art.

FIGS. 1-3 depict the types of problems that may be encountered by traditional implants P1 with teeth P80 or sharp surface features, for example, protruding from an integration surface. FIG. 1A depicts a perspective view and FIG. 1B depicts a side view of an example of a traditional implant P1 having sharp, protruding teeth P80 on the top surface P10 and the bottom surface P20 of the implant P1. FIGS. 1A and 1B shows an array of teeth P80 each having a square pyramid shape, but any shape, number, or arrangement of sharp, protruding teeth P80 may cause a problem. The terminus of these sharp, protruding teeth P80 may be a point or other sharp or jagged area.

FIG. 2 shows an example of the damage that may occur to a vertebral endplate P25 during and after insertion of an implant P1 having teeth P80, for example, when the implant P1 is seated between vertebrae using impact forces. FIG. 2(a) shows the condition of the endplate P25 prior to implantation. FIG. 2(b) shows the effect on the vertebral endplate P25 when the implant P1 of FIG. 1A is implanted or force fit into the joint space. FIG. 2(c) illustrates the type of damage that may result to the vertebral endplate P25 due to implant teeth P80. As is evident, the protruding teeth P80 damage, scribe, and degrade the vertebral endplate P25 by causing a number of grooves or ridges in the vertebrae where the teeth P80 contact the surface of the vertebral endplate 25. This scribing can also significantly reduce the amount of expulsion resisting friction as the teeth are aligned in the direction of implantation and as the first feature cuts a path into the endplate the subsequent teeth follow in the cut channel and have no bone behind them to act against the expulsion forces. Although not shown, a similar result may occur from the top surface P10 of the implant P1 contacting an upper vertebral endplate 25.

Aside from severe damage that may be caused during implantation, additional damage may occur after implantation has occurred. For example, after implantation, the bone may dissolve and remodel as the bone is overloaded. FIG. 3 depicts the type of damage that may occur under a focused load on the implant P1 once inserted into position. FIG. 3(a) shows the implant P1 in contact with the vertebral endplate P25 once implanted. It is noted that the implant P1 may be unstable during implantation because only the points of the teeth directly contact the bone. Thus, the implant P1 may be subject to movement (e.g., side to side, front to back, or twisting) due to the poor contact with the bone structure. FIG. 3(b) shows the effect of bone remodeling as the sharp teeth P80 continue to press on the vertebrae under the load and over time. FIG. 3(c) depicts the type of resulting damage P26 that may occur after some period of time of continued load on the vertebral endplate P25. FIG. 3(d) depicts the vertebrae with the implant P1 removed and the amount of damage P26 which may be caused to the vertebral endplate P25.

Avoiding such teeth and the attendant risk of damage, the integration surfaces of the present invention do not have teeth, undercuts, or other sharp, potentially damaging structures; rather, the integration surfaces have a pattern of repeating features of predetermined sizes, smooth shapes, and orientations. In particular, the integration surfaces comprise an organized arrangement of predefined surface features that provide one or more of the following functions: (a) engage the vertebral endplates with a friction fit; (b) attain initial stabilization during implantation; (c) attain permanent stabilization once implanted; (d) evenly distribute and disperse the load across the implant from the vertebral endplates; (e) do not damage the vertebral endplates (e.g., do not shave, shear, or remodel the endplates during or after implantation); and (f) benefit fusion.

The integration surface may include the top surface, the bottom surface, or both surfaces of the implant 1. In the case of no integration plates 82, this would include the top 10, bottom 20, or both surfaces of the body 2 of the implant 1. In the case of one integration plate 82 affixed to the top 10 of the body 2 of the implant 1, this would include the top 81 of the integration plate 82, the bottom 20 of the body 2, or both surfaces. In the case of one integration plate 82 affixed to the bottom 20 of the body 2 of the implant 1, this would include the top 10 of the body 2, the top 81 of the integration plate 82 (i.e., the outer surface of the integration plate 82 at the bottom of the implant), or both surfaces. In the case of two integration plates 82 sandwiched around the body 2 of the implant 1, this would include the top 81 of the first integration plate 82, the top 81 of the second integration plate 82, or both surfaces (i.e., the outer surfaces of both integration plates 82 at the top and bottom of the implant 1, respectively).

The integration surface preferably includes a predetermined repeating pattern formed of at least three at least partially overlapping repeated patterns. As used in this document, "predetermined" means determined beforehand, so that the predetermined characteristic must be determined, i.e., chosen or at least known, before use of the implant. The design may produce surfaces that resist motion induced by loading in specific directions that are beneficial to the installation process and resist the opposing forces that can be the result of biologic or patient activities such as standing, bending, or turning or as a result of other activities. The shapes of the surface features, when overlapping, work to increase the surface contact area but do not result in undercuts that generate a cutting or aggressively abrasive action on the contacting bone surfaces.

The repeating pattern is formed of at least three at least partially overlapping repeating patterns comprising a first repeating pattern 103, a second repeating pattern 105, and a third repeating pattern 107. The repeating pattern may include any number of patterns, three or more, as is necessary to achieve the desired surface structure. By overlapping, it is intended that the first repeating pattern 103 and second repeating pattern 105, the second repeating pattern 105 and third repeating pattern 107, the first repeating pattern 103 and third repeating pattern 107, all three patterns, or any subsequent patterns at least partially contact one another and overlay the other pattern or patterns.

Each of the patterns may include a designed configuration of surface features including recesses or protrusions in a shape, such as dots, circles, semi-circles, spheres, semi-spheres, squares, cubes, polyhedral pyramids, triangles, lines, strips, amorphous shapes, or any suitable pattern designed to not align with the direction of implantation, provide frictional contact with opposing bones, and disperse loading. In one embodiment, the patterns include a plurality of recesses in the shape of spheres or semi-spheres.

Figure 5:
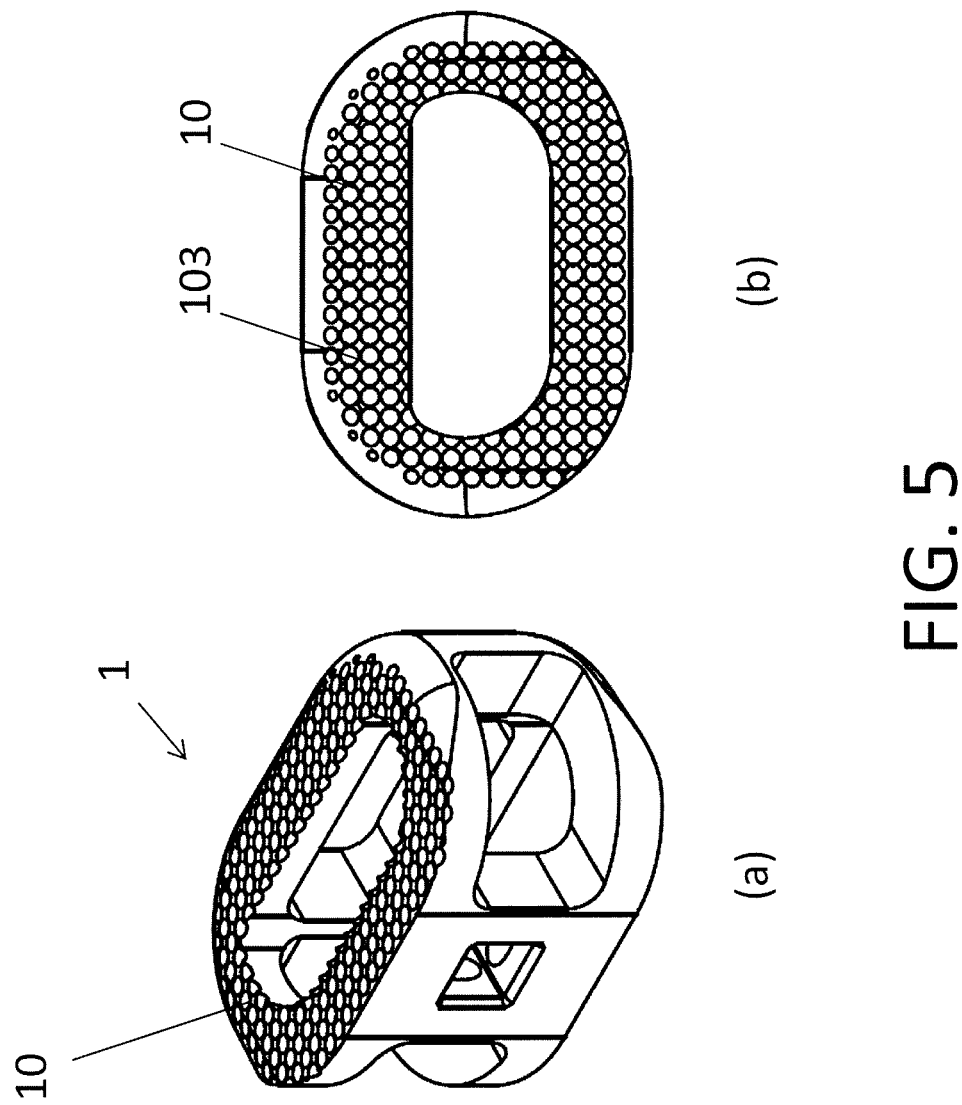
FIG. 5 shows (a) a perspective view and (b) a top view of an embodiment of the interbody spinal implant having a first pattern on an integration surface.
Figure 6:
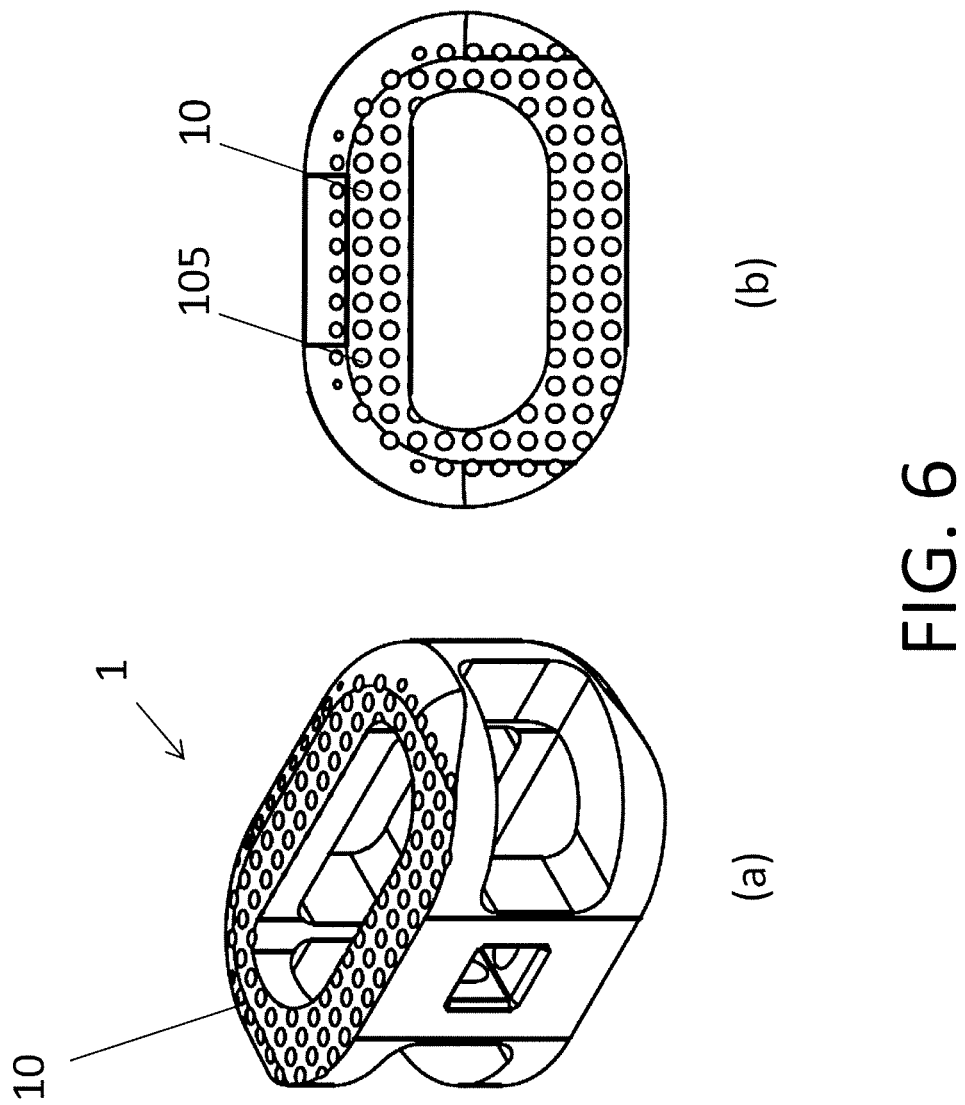
FIG. 6 shows (a) a perspective view and (b) a top view of an embodiment of the interbody spinal implant having a second pattern on an integration surface.
Figure 7:
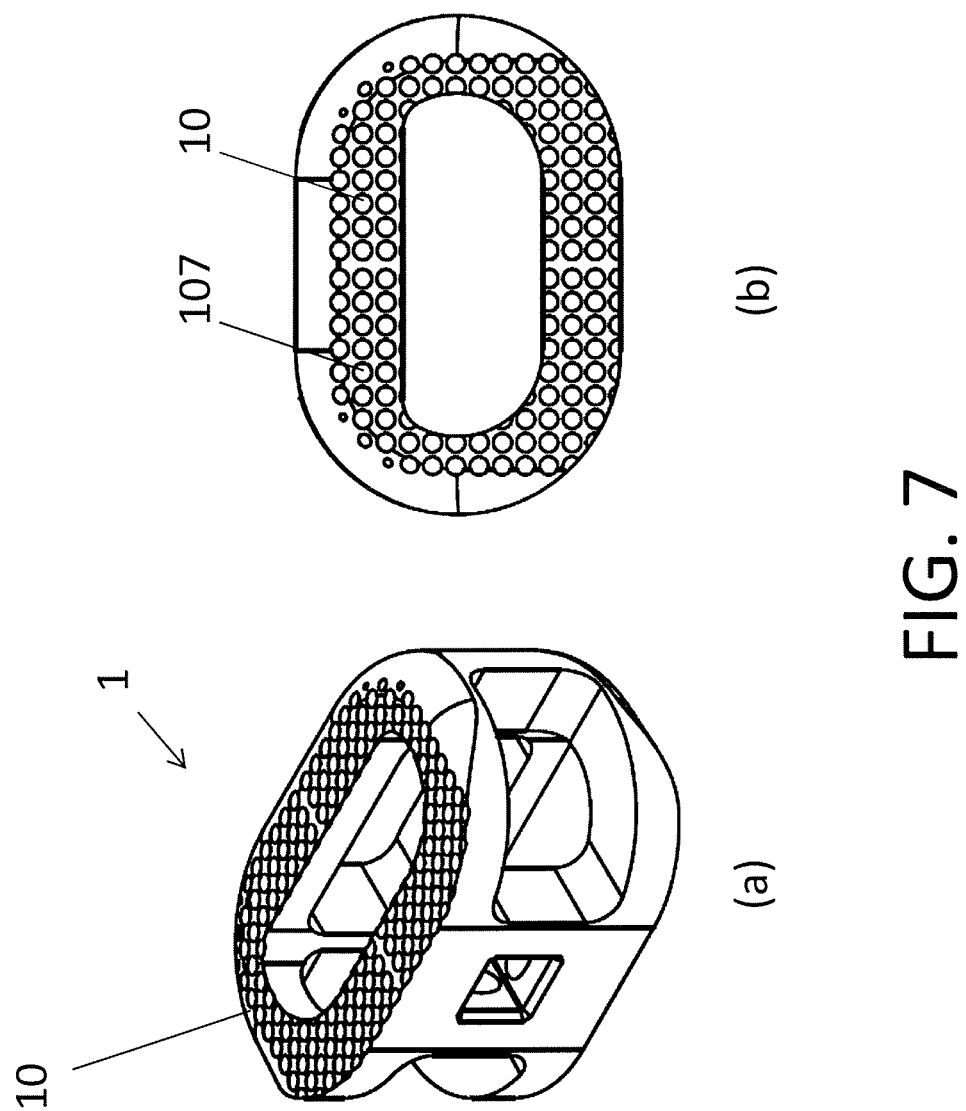
FIG. 7 shows (a) a perspective view and (b) a top view of an embodiment of the interbody spinal implant having a third pattern on an integration surface.
Figure 11:
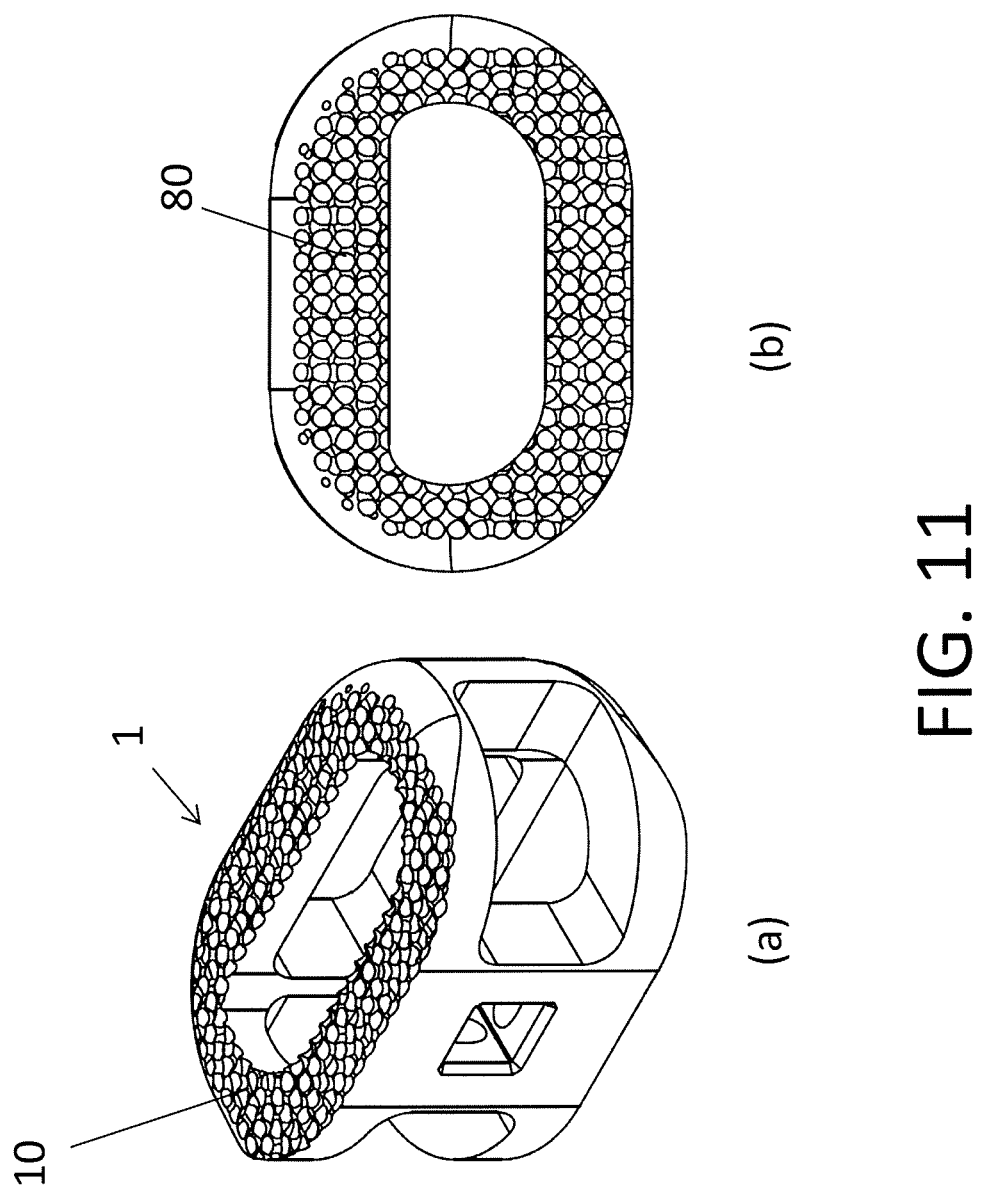
FIG. 11 shows (a) a perspective view and (b) a top view of an embodiment of the interbody spinal implant having first, second, and third patterns on an integration surface.

The pattern may consist of an array of shapes or structures. The array may include a systematic arrangement of recesses or objects in rows, columns, or both. FIG. 5 depicts an example of a first repeating pattern 103 arranged as an array (e.g., columns and rows) of spherical shapes. FIG. 6 depicts an example of a second repeating pattern 105 arranged as an array (e.g., columns and rows) of spherical shapes. FIG. 7 depicts an example of a third repeating pattern 107 arranged as an array (e.g., columns and rows) of spherical shapes. FIG. 11 depicts the resulting pattern (e.g., a roughened surface topography 80) of overlapping the patterns shown in FIGS. 5, 6, and 7.

Figure 8:
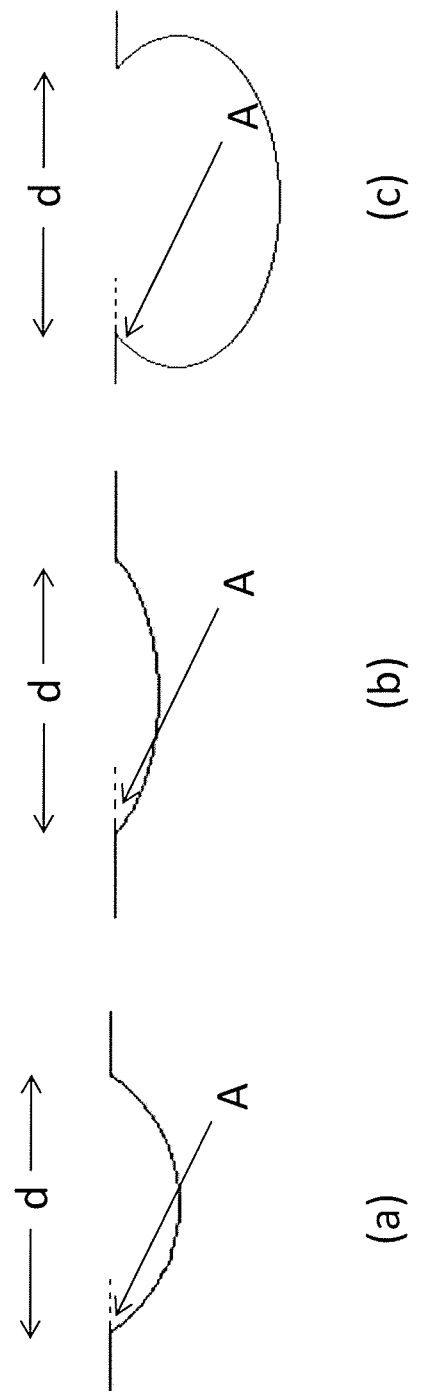
FIG. 8 shows three types of recesses having the same diameter with varying slopes.
Figure 9:
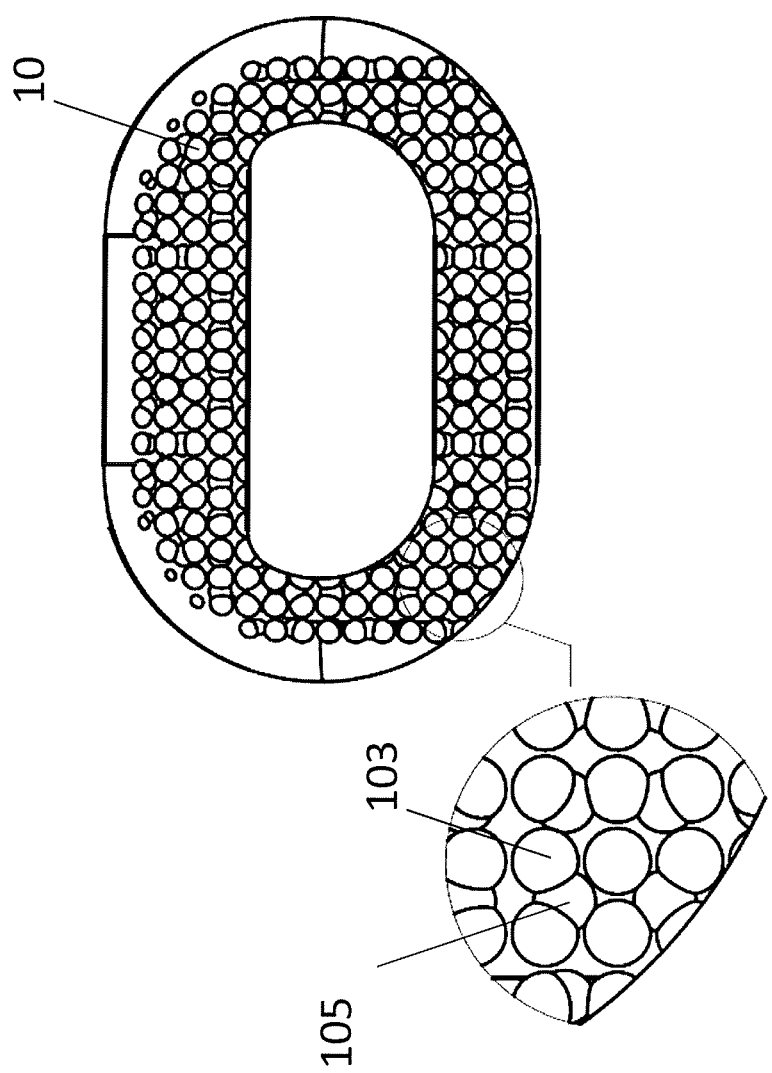
FIG. 9 shows a pattern generated by a partial overlap of the first and second patterns shown in FIGS. 5 and 6, respectively.
Figure 10:
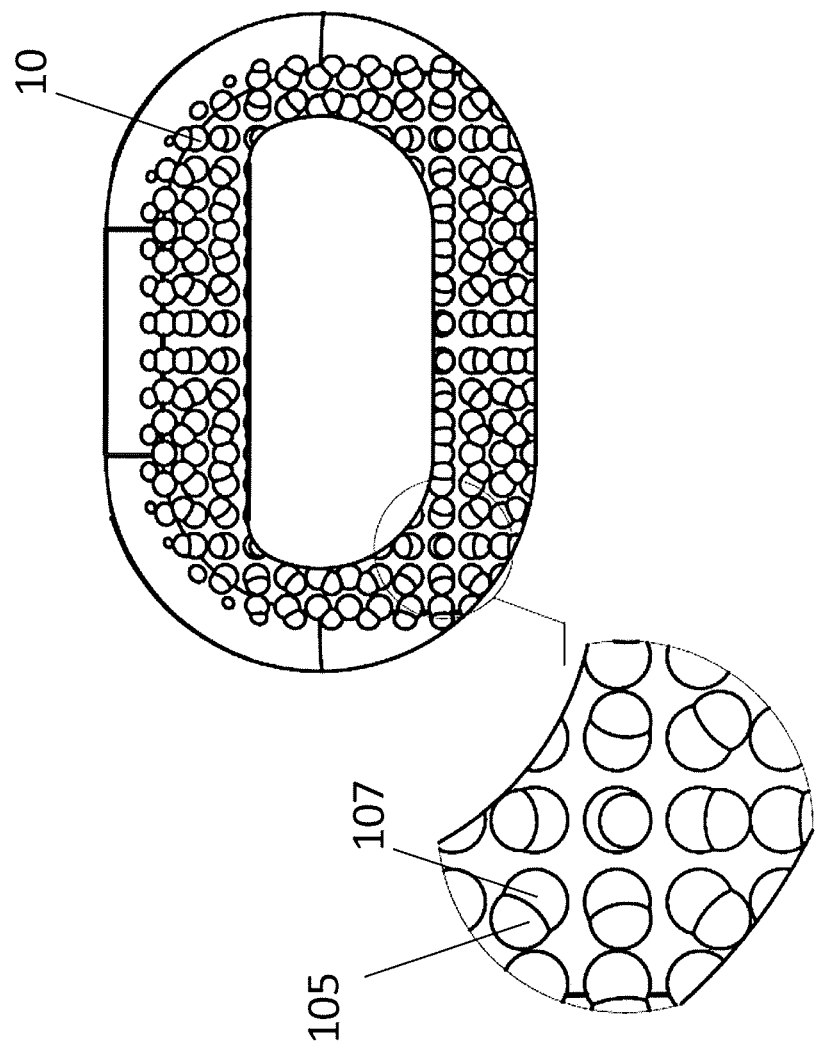
FIG. 10 shows a pattern generated by a partial overlap of the second and third patterns shown in FIGS. 6 and 7, respectively.

The pattern may also include a radial pattern. In other words, subsequent patterns may radiate outward at a fixed distance from one or more points from a first or previous pattern. The pattern may radiate from a point by shifting the second repeating pattern 105 and the third repeating pattern 107 (or subsequent patterns) in the x-axis, the y-axis, or both the x-axis and y-axis. For example, the second repeating pattern 105, the third repeating pattern 107, or both repeating patterns may radiate at a fixed distance from at least one point defined by the first repeating pattern 103. FIG. 9 depicts the first repeating pattern 103 and the second repeating pattern 105 from FIGS. 6 and 7, respectively, where the second repeating pattern 105 radiates at a fixed distance in both the x- and y-axis from the first repeating pattern 103. FIG. 10 depicts the second repeating pattern 105 and third repeating pattern 107 from FIGS. 7 and 8, respectively, where the third pattern 107 radiates at a fixed distance in both the x- and y-axis from the first repeating pattern 103 and the second repeating pattern 105.

Each of the three repeating patterns preferably contains no sharp points or undercuts. Sharp points and undercuts may be avoided, for example, by forming recesses having a slope of less than 90° relative to the integration surface. The slope is measured based on the angle A of the side of the recess (e.g., a tangent line) as compared to the plane of the integration surface (e.g., the integration surface equals 0°). FIGS. 8(a) and (b) depict examples of recesses having slopes of less than 90° relative to the integration surface (e.g., about 20° and about 10°, respectively). FIG. 8(c) shows an example of a recess having a slope greater than 90° (e.g., about 130°), which produces an undercut or sharp point not in accordance with the present invention. As will be evident to one of ordinary skill in the art, the slope of the recess may be controlled based on the shape of the recess, the depth of the recess, and the diameter of the recess. FIGS. 8(a), (b), and (c) each comprise the same diameter d recess, but each recess has a different depth, different angle A, and thus a different slope. FIG. 8(c) has the greatest depth and the greatest angle A, which at more than 90° produces an undesired undercut. FIG. 8(b) has the smallest depth and the smallest angle A. FIG. 8(c) is greater in depth than FIG. 8(b) and thus produces a bigger angle A and greater slope.

Preferably, each of the repeating patterns have recesses with slopes of 30° or less, 25° or less, 20° or less, 15° or less, 10° or less, or 5° or less based on the integration surface. In one embodiment, the first repeating pattern 103 includes recesses having a slope of 30° or less relative to the integration surface, the second repeating pattern 105 includes recesses having a slope of 25° or less relative to the integration surface, and the third repeating pattern 107 includes recesses having a slope of 20° or less relative to the integration surface.

The patterns may include recesses having the same or varying diameters, depths, and spacings. In one embodiment, the three repeating patterns each comprise spheres or semi-spheres having varying diameters. In another embodiment, the first repeating pattern 103 has the greatest depth, the second repeating pattern 105 has an intermediate depth, and the third repeating pattern 107 has the smallest depth. In yet another embodiment, the spacing of the at least three repeating patterns may be as follows: the first repeating pattern 103 may have a spacing S1, the second repeating pattern 105 may have a spacing S2, and the third repeating pattern 107 may have a spacing S3, where the spacing S1 is less than the spacing S3 which, in turn, is less than the spacing S2. The spacing may be based on the spacing between each of the recesses or protrusions in the pattern (e.g., a distance from center point to center point of each recess along the x-axis and y-axis). Preferably, each of the three repeating patterns have features with diameters, depths, and spacings which are sequentially sized and positioned to preserve an amount of the features and patterns from the previous pattern or patterns.

These designed surfaces are composed of various sizes of features that may interact, at the microscopic level, with the tissues and stimulate their natural remodeling and growth. At a larger scale these features perform the function of generating non-stressful friction that allows for a friction fit that does not abrade, chip, perforate, or compromise the critical endplate structures. Preferably, the surface features are uni-directionally oriented such that the implant may be inserted in one direction but cannot back out once implanted (e.g., resist expulsion).

The overlapping of the three patterns can be achieved using manufacturing processes that are completed sequentially and, therefore, do not remove or degrade the previous method. The shapes of the surface protrusions or recesses may be formed by a subtractive process, an additive process, or both processes. The shapes may be formed using processes and methods commonly applied to remove material (e.g., subtractive techniques) during fabrication of implantable devices such as chemical, electrical, electrochemical, plasma, or laser etching; cutting and removal processes; casting; forging; machining; drilling; grinding; shot peening; abrasive media blasting (such as sand or grit blasting); combinations of these subtractive processes; and others known in the art. Alternatively or in addition, the shapes may be formed using methods commonly applied to add material (e.g., additive processes) to a surface such as welding, thermal, coating, sputtering, printing, optical melt additive processes, and other additive processes known in the art.

Figure 18:
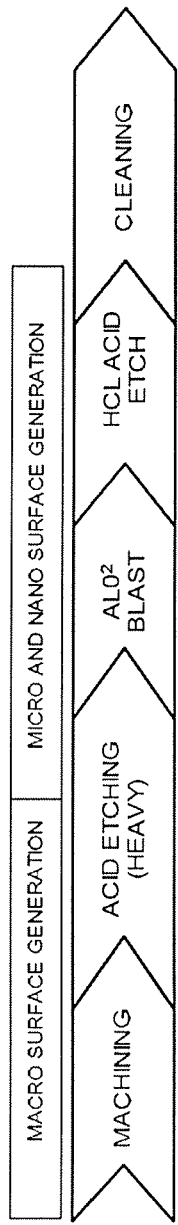
FIG. 18 illustrates examples of types of process steps that can be used to form macro, micro, or nano processes.

The additive or subtractive process may include macro, micro, or nano surface features. FIG. 18 illustrates one set of process steps that can be used to form macro, micro, or nano features. The term "macro" typically means relatively large; for example, in the present application, dimensions measured in millimeters (mm). The term "micro" typically means one millionth ($10^{-6}$); for example, in the present application, dimensions measured in microns (μm) which correspond to $10^{-6}$ meters. The term "nano" typically means one billionth ($10^{-9}$); for example, in the present application, dimensions measured in nanometers (nm) which correspond to $10^{-9}$ meters. As illustrated in FIG. 18, there may be some overlap in the processes that can be applied to form each of the three types of features (macro, micro, and nano). For example, acid etching can be used to form the macro features, then the same or a different acid etching process may be used to form micro features.

Preferably, the at least three repeating patterns are formed of macro-sized features (although it is contemplated that micro- and nano-sized features may also be included). The macro features are relatively large features (e.g., on the order of millimeters). Preferably, the macro features are formed by subtractive techniques, which remove at least portions of the surface (e.g., from the titanium material that was used to form the part). Suitable subtractive techniques may include, for example, machining (e.g., machine tools, such as saws, lathes, milling machines, and drill presses, are used with a sharp cutting tool to physically remove material to achieve a desired geometry) or unmasked or masked etching (e.g., portions of the surface are protected by a masking material which resists etching and an etching substance is applied to unmasked portions).

For example, the three repeating patterns may include overlapping patterns shown in FIGS. 5-7 and 9-11. FIG. 5 illustrates the result of one step or a first step in forming macro features. Specifically, a first pattern 103 of the macro features is cut or formed in a surface (e.g., the top surface 81 of an integration plate 82). FIG. 6 illustrates the result of a second step in forming macro features. Specifically, a second pattern 105 of the macro features is cut or formed in the surface. FIG. 7 illustrates the result of the third step in forming macro features. Specifically, a third pattern 107 of the macro features may be cut or formed in the surface. In one embodiment, the process includes forming first-cut surface features having a spacing 51 and a greatest depth; forming second-cut surface features having a spacing S2 and an intermediate depth; and forming third-cut surface features having a spacing S3 and a smallest depth, where the spacing S1<spacing S3<spacing S2.

Following completion of the three, sequential processing steps, the finished macro features may comprise multiple patterns of the three, overlapping cuts: the first pattern 103, the second pattern 105, and the third pattern 107, for example, as depicted as the roughened surface topography 80 in FIG. 11. Together, the "cut 1" features of the first pattern 103, the "cut 2" features of the second pattern 105, and the "cut 3" features of the third pattern 107 may cover about 95% of the total area of the surface, for example, leaving about 5% of the original surface remaining. Preferably, the surface features cover about 97% of the total area of the surface. Even more preferably, the at least three repeating patterns cover substantially all of the integration surface.

As should be readily apparent to a skilled artisan, the process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the surface topography desired, for example, the integration surface of the implant 1 may be oriented in opposition to the biologic forces on the implant 1 and to the insertion direction. In one particular embodiment, for example, the pattern of the roughened surface topography 80 may be modeled after an S-shaped tire tread. It is also contemplated that the same or different process steps may be used to create each of the features on each of the desired surfaces.

Roughness Parameters

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. Each parameter is explained in detail as follows.

1. Average Amplitude Ra

Figure 19:
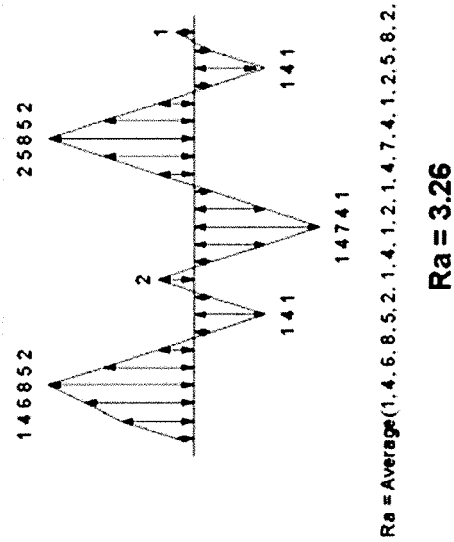
FIG. 19 graphically represents the average amplitude, Ra.

In practice, "Ra" is the most commonly used roughness parameter. It is the arithmetic average height. Mathematically, Ra is computed as the average distance between each roughness profile point and the mean line. In FIG. 19, the average amplitude is the average length of the arrows.

In mathematical terms, this process can be represented as $$Ra = \frac{1}{n}\sum_{i=1}^{n} |y_i|$$

2. Average Peak-to-Valley Roughness Rz

Figure 20:
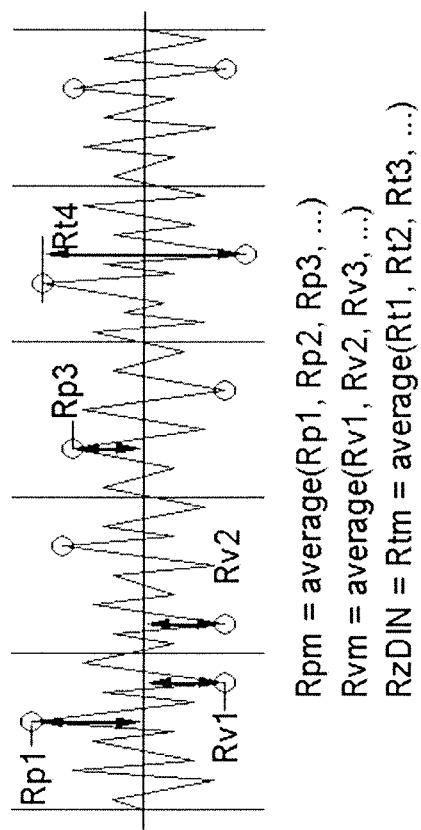
FIG. 20 graphically represents the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 20.

3. Maximum Peak-to-Valley Height Rmax

Figure 21:
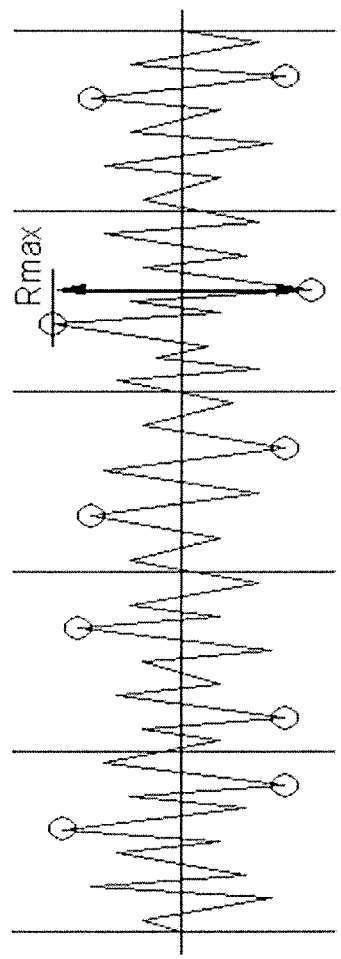
FIG. 21 graphically represents the maximum peak-to-valley height, Rmax.

The maximum peak-to-valley height, Rmax, is the maximum peak-to-valley distance in a single sampling length—as illustrated in FIG. 21.

4. Total Peak-to-Valley of Waviness Profile Wt

Figure 22:
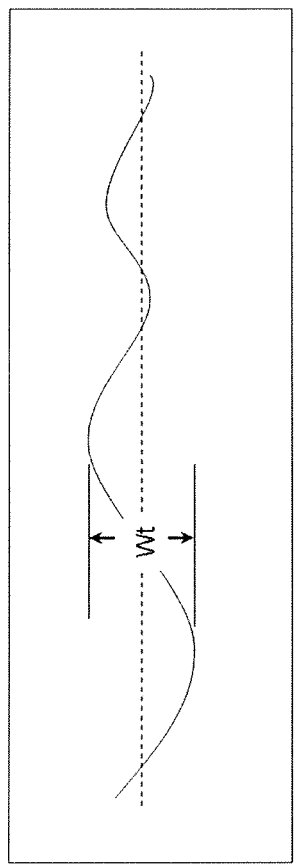
FIG. 22 graphically represents the total peak-to-valley of waviness profile.

The total peak-to-valley of waviness profile (over the entire assessment length) is illustrated in FIG. 22.

5. Mean Spacing Sm

Figure 23:
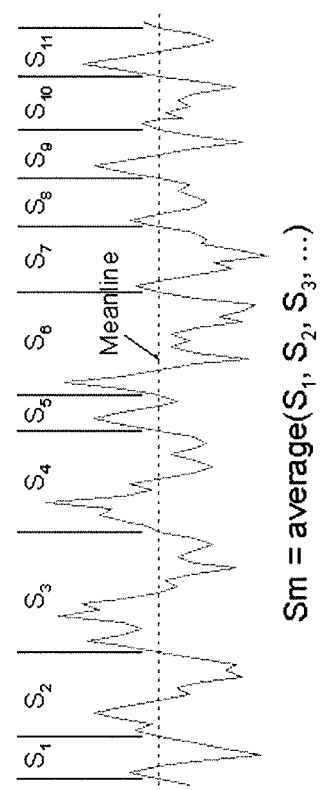
FIG. 23 graphically represents the mean spacing, Sm.

The mean spacing, Sm, is the average spacing between positive mean line crossings. The distance between each positive (upward) mean line crossing is determined and the average value is calculated, as illustrated in FIG. 23.

The parameters Sm, Rmax, and Ra can be used define the surface roughness following formation of each of the three types of macro features.

The following preferred ranges (all measurements in microns) are as follows for the macro features for each of the three parameters. The mean spacing, Sm, is between about 400-2,000, with a range of 750-1,750 preferred and a range of 1,000-1,500 most preferred. The maximum peak-to-valley height, Rmax, is between about 40-500, with a range of 150-400 preferred and a range of 250-300 most preferred. The average amplitude, Ra, is between about 8-200, preferably, 20-200, more preferably 50-150, and most preferably 100-125.

An example of such data is provided in the Table below.

TABLE

| Surface Feature Size and Roughness (Metric): Macro (μm) | | |
|---|---|---|
| Size (Sm) | Depth (Rmax) | Roughness (Ra) |
| Max. 2,000 | 500 | 200 |
| Min. 400 | 40 | 20 |
| Avg. 1,200 | 270 | 110 |

Integration Plate and Attachment

In the case of a composite implant 1, 101, 101a, 201, and 301, the integration plate, shown in the drawing as component 82 (FIGS. 12 and 13), 182a (FIG. 14), 182 (FIG. 15), 382 (FIG. 16), and 282 (FIG. 17), respectively, includes the roughened surface topography 80, 180, 180a, 280, and 380 for the integration surface, and is connectable to either or both of the top surface 10, 110, 110a, 210, and 310 or bottom surface 20, 120, 120a, 220, and 320. The integration plate 82, 182, 182a, 282, and 382 includes a top surface 81, 181, 181a, 281, and 381; a bottom surface 83, 183, 183a, 283, and 383; an anterior portion 41, 141, 141a, 241, and 341; a posterior portion 51, 151, 151a, 251, and 351; and at least one vertical aperture 61, 161, 161a, 261, and 361. The anterior portion 41, 141, 141a, 241, and 341 preferably aligns with the anterior portion 40, 140, 140a, 240, and 340 of the main body 2 of the implant 1, 101, 101a, 201, and 301, respectively, and the posterior portion 51, 151, 151a, 251, and 351 aligns with the posterior portion 50, 150, 150a, 250, and 350 of the main body 2 of the implant 1, 101, 101a, 201, and 301, respectively. The vertical aperture 61, 161, 161a, 261, and 361 preferably aligns with the vertical aperture 60, 160, 160a, 260, and 360 of the main body 2 of the implant 1, 101, 101a, 201, and 301, respectively. Thus, the integration plate vertical aperture 61, 161, 161a, 261, and 361 and the body vertical aperture 60, 160, 160a, 260, and 360 preferably comprise substantially the same shape.

The integration plate 82, 182, 182a, 282, and 382 may be attached or affixed to the main body of the implant 1, 101, 101a, 201, and 301 using any suitable mechanisms known in the art. For example, the bottom surface 83, 183, 183a, 283, and 383 of the integration plate 82, 182, 182a, 282, and 382 may comprise a reciprocal connector structure, such as a plurality of posts 84, 184, 184a, 284, and 384 that align with and insert into a corresponding connector structure such as a plurality of holes 12, 112, 112a, 212, and 312 on the top surface 10, 110, 110a, 210, and 310 and/or bottom surface 20, 120, 120a, 220, and 320 of the main body 2 of the implant 1, 101, 101a, 201, and 301, respectively, and thus facilitate the connection between the integration plate 82, 182, 182a, 282, and 382 and the main body 2 of the implant 1, 101, 101a, 201, and 301. Thus, integration plates 82, 182, 182a, 282, and 382 with different sizes, shapes, or features may be used in connection with the implant 1, 101, 101a, 201, and 301, for example, to accommodate attributes of the spine of the patient into which the implant 1, 101, 101a, 201, and 301 is to be implanted. Among these different sizes, shapes, and features are lordotic angles; anti-expulsion edges 8, 108, 108a, 208, and 308; and anti-expulsion angles as described throughout this specification.

The implant 1, 101, 101a, 201, and 301 is configured to receive the integration plate 82, 182, 182a, 282, and 382, respectively. Thus, for example, the top surface 10, 110, 110a, 210, and 310 and/or bottom surface 20, 120, 120a, 220, and 320 of the implant 1, 101, 101a, 201, and 301 may be optionally recessed, and comprise a plurality of holes 12, 112, 112a, 212, and 312 that mate with the plurality of posts 84, 184, 184a, 284, and 384 on the bottom surface 83, 183, 183a, 283, and 383 of the integration plate 82, 182, 182a, 282, and 382. Thus, the plurality of posts 84, 184, 184a, 284, and 384 are inserted into the plurality of holes 12, 112, 112a, 212, and 312.

FIG. 5 shows that the top surface 10 is recessed and comprises a plurality of holes 12, but the recessed bottom surface 20 and its holes 12 are not shown. FIG. 7 shows that the top surface 110a is recessed and comprises a plurality of holes 112a, but the recessed bottom surface 120a and its holes 112a are not shown. FIG. 9 shows that the top surface 110 is recessed and comprises a plurality of holes 112, but the recessed bottom surface 120 and its holes 112 are not shown. FIG. 10 shows that the top surface 310 is recessed and comprises a plurality of holes 312, but the recessed bottom surface 320 and its holes 312 are not shown. FIG. 11 shows that the top surface 210 is recessed and comprises a plurality of holes 212, but the recessed bottom surface 220 and its holes 212 are not shown. The recess may be at a depth D, and the recess depth D preferably is uniform throughout the top surface 10, 110, 110a, 210, and 310 and/or bottom surface 20, 120, 120a, 220, and 320.

The recess depth D preferably corresponds to a thickness T of the integration plate 82, 182, 182a, 282, and 382. Thus, in some aspects, the depth D and thickness T are the same so that once the integration plate 82, 182, 182a, 282, and 382 and body of the implant 1, 101, 101a, 201, and 301, respectively, are placed together, the top surface 10, 110, 110a, 210, and 310 and/or bottom surface 20, 120, 120a, 220, and 320 of the implant 1, 101, 101a, 201, and 301 is substantially even, at least at the seam/junction between the integration plate 82, 182, 182a, 282, and 382 and the top surface 10, 110, 110a, 210, and 310 or bottom surface 20, 210, 120a, 220, and 320. In some embodiments, the posterior portion 51, 151, 151a, 251, and 351 and the anterior portion 41, 141, 141a, 241, and 341 of the integration plate 82, 182, 182a, 282, and 382 have different thicknesses such that the anterior portion 41, 141, 141a, 241, and 341 has a greater thickness than the thickness of the posterior portion 51, 151, 151a, 251, and 351.

The recess depth D and the thickness T may each independently be from about 0.1 mm to about 10 mm. In preferred aspects, the recess depth D and the thickness T may each independently be from about 1 mm to about 5 mm. Thus, for example, the recess depth D or the thickness T may be selected from about 0.1 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, 5.5 mm, about 6 mm, about 6.5 mm, about 7 mm, about 75 mm, or about 8 mm.

Recessing the top surface 10, 110, 110a, 210, and 310 or bottom surface 20, 120, 120a, 220, and 320 exposes a ridge 11, 111, 111a, 211, and 311 against which the anterior portion 41, 141, 141a, 241, and 341; posterior portion 51, 151, 151a, 251, and 251; or lateral side of the integration plate 82, 182, 182a, 282, and 382 may be seated when brought together with the implant 1, 101, 101a, 201, and 301.

The integration plate 82, 182, 182a, 282, and 382 may be used with an implant suitable for ALIF (e.g., implant 1, integration plate 82), PLIF (e.g., implant 101, integration plate 182), or TLIF fusion (e.g., implant 101a, integration plate 182a); may be used with an implant suitable for cervical fusion (e.g., implant 201, integration plate 282); and may be used with an implant suitable for lateral lumbar insertion (e.g., implant 301, integration plate 382).

The reciprocal connector such as the post 84, 184, 184a, 284, and 384 preferably is secured within the connector of the body such as the hole 12, 112, 112a, 212, and 312 to mediate the connection between the integration plate 82, 182, 182a, 282, and 382 and the implant 1, 101, 101a, 201, and 301. The connection should be capable of withstanding significant loads and shear forces when implanted in the spine of the patient. The connection between the post 84, 184, 184a, 284, and 384 and the hole 12, 112, 112a, 212, and 312 may comprise a friction fit. In some aspects, the reciprocal connector such as the post 84, 184, 184a, 284, and 384 and the connector of the body such as the hole 12, 112, 112a, 212, and 312 have additional compatible structures and features to further strengthen the connection between the integration plate 82, 182, 182a, 282, and 382 and the implant 1, 101, 101a, 201, and 301.

The structures and features may be on either or both of the integration plate 82, 182, 182a, 282, and 382 and the main body 2 of the implant 1, 101, 101a, 201, and 301. In general, the structures include fasteners, compatibly shaped joints, compatibly shaped undercuts, and/or other suitable connectors having different shapes, sizes, and configurations. For example, a fastener may include a pin, screw, bolt, rod, anchor, snap, clasp, clip, clamp, or rivet. In some aspects, an adhesive may be used to further strengthen any of the integration plate 82, 182, 182a, 282, and 382 and implant 1, 101, 101a, 201, and 301 connections described in this specification. An adhesive may comprise cement, glue, polymer, epoxy, solder, weld, or other suitable binding materials.

The integration plate 82, 182, 182a, 282, and 382 may comprise one or more reciprocal connectors (not shown), such as one or more posts, each having a bore, extending through a horizontal plane. The post may be inserted into a connector such as a hole through the implant 1, 101, 101a, 201, and 301. A fastener (not shown), such as a pin, may be inserted through the bore thereby preventing the post from being disengaged from the hole. In some aspects, the pin may be threaded through a second bore that passes through the walls of the implant 1, 101, 101a, 201, and 301 itself; although it is preferable that the implant 1, 101, 101a, 201, and 301 does not include a second bore through its walls and that the bore is accessible from the space inside of the implant. Alternatively, the integration plate 82, 182, 182a, 282, and 382 may comprise a plurality of bores (not shown) present on and having openings accessible from the bottom of the integration plate 82, 182, 182a, 282, and 382. The bores may mate with a plurality of fasteners, which may comprise rods integral with or otherwise attached to the top surface or bottom surface of the implant 1, 101, 101a, 201, and 301. For example, the rods may be molded as upward-facing extensions or snap-fit into the bores. In some aspects, for example, where the body 2 of the implant 1, 101, 101a, 201, and 301 is comprised of a plastic or polymeric material, the hole 12, 112, 112a, 212, and 312 may not be present, and the screw or bolt (not shown) may be screwed directly into the plastic or polymeric material, with the screw threads tightly gripping the plastic or polymeric material to form the connection.

It is also contemplated that the bottom surface 83, 183, 183a, 283, and 383 of the integration plate 82, 182, 182a, 282, and 382 may comprise undercuts (not shown) in shapes that form a tight junction with compatible shapes on the implant 1, 101, 101a, 201, and 301. For example, the bottom surface 83, 183, 183a, 283, and 383 may comprise a dovetail joint, bevel, or taper that fits with a counterpart dovetail joint, bevel, or taper on the body 2 of the implant 1, 101, 101a, 201, and 301.

An adhesive (not shown) may directly join the integration plate 82, 182, 182a, 282, and 382 and the body 2 of the implant 1, 101, 101a, 201, and 301 together, with or without other connecting features. For example, the adhesive may be applied to the bottom surface 83, 183, 183a, 283, and 383 of the integration plate 82, 182, 182a, 282, and 382. Alternatively, the adhesive may be applied to the top surface 10, 110, 110a, 210, and 310; the bottom surface 20, 120, 120a, 220, and 320; or both surfaces of the implant 1, 101, 101a, 201, and 301.

The foregoing describes various non-limiting examples of how the one or two integration plates 82, 182, 182a, 282, and 382 may be joined together with the implant 1, 101, 101a, 201, and 301.

Other Implant Features

The implant 1 may comprise some or all of the following implant features. In some aspects, the interbody spinal implant 1 is substantially hollow and has a generally oval-shaped transverse cross-sectional area with smooth, rounded, or both smooth and rounded lateral sides 30 and posterior-lateral corners. The implant 1 includes at least one vertical aperture 60 that extends the entire height of the implant body 2. The vertical aperture 60 defines an interior surface 60a or hollow cavity within the implant 1, which may be filled with bone growth-inducing materials. The vertical aperture (a) extends from the top surface to the bottom surface, (b) has a size and shape predetermined to maximize the surface area of the top surface and the bottom surface available proximate the anterior and posterior portions while maximizing both radiographic visualization and access to the substantially hollow center, and (c) optionally defines a transverse rim. The vertical aperture 60 may further define a transverse rim 100 having a greater posterior portion thickness 55 than an anterior portion thickness 45.

In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40.

The implant 1 may be shaped to reduce the risk of subsidence, and improve stability, by maximizing contact with the apophyseal rim of vertebral endplates. Embodiments may be provided in a variety of anatomical footprints. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim.

The implant 1 may include other surface features including soft tissue surfaces. The soft tissue surface or insertion surface may include a low friction or smooth surface to avoid unintentional laceration or abrasion of delicate soft tissues the implant 1 contacts during insertion, after insertion, or both. The soft tissue surface may include any outer surfaces, other than the one or more integration surfaces, which may contact bone or soft tissues during or after implantation.

As illustrated in FIG. 4A and FIG. 12, the implant 1 may have an opening 90 in the anterior portion 40. In one embodiment, the posterior portion 50 may have a similarly shaped opening 90 (not shown). In some aspects, only the anterior portion 40 has the opening 90 while the posterior portion 50 has an alternative opening 92 (which may have a size and shape different from the opening 90). The opening 92 defines an interior surface or hollow cavity, which may be filled with bone growth-inducing materials. The interior surfaces defined by these openings may define graft retaining surfaces.

The opening 90, 290, and 390 has a number of functions. One function is to facilitate manipulation of the implant 1, 201, and 301 by the caretaker. Thus, the caretaker may insert a surgical tool into the opening 90, 290, and 390 and, through the engagement between the surgical tool and the opening 90, 290, and 390, manipulate the implant 1, 201, and 301. The opening 90, 290, and 390 may be threaded to enhance the engagement. A suitable surgical tool, such as a distractor (not shown), may be selected by one of ordinary skill in the art.

Figure 14:
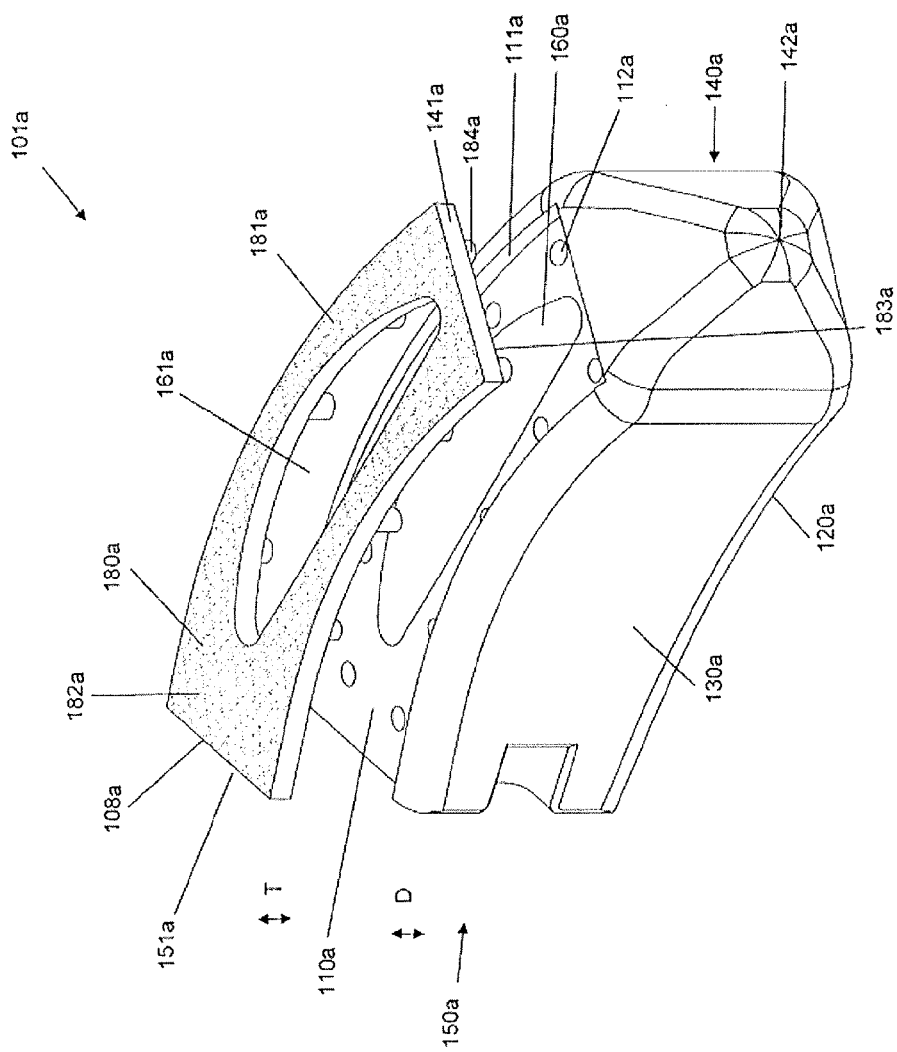
FIG. 14 shows an exploded view of a curved implant with an integration plate.
Figure 15:
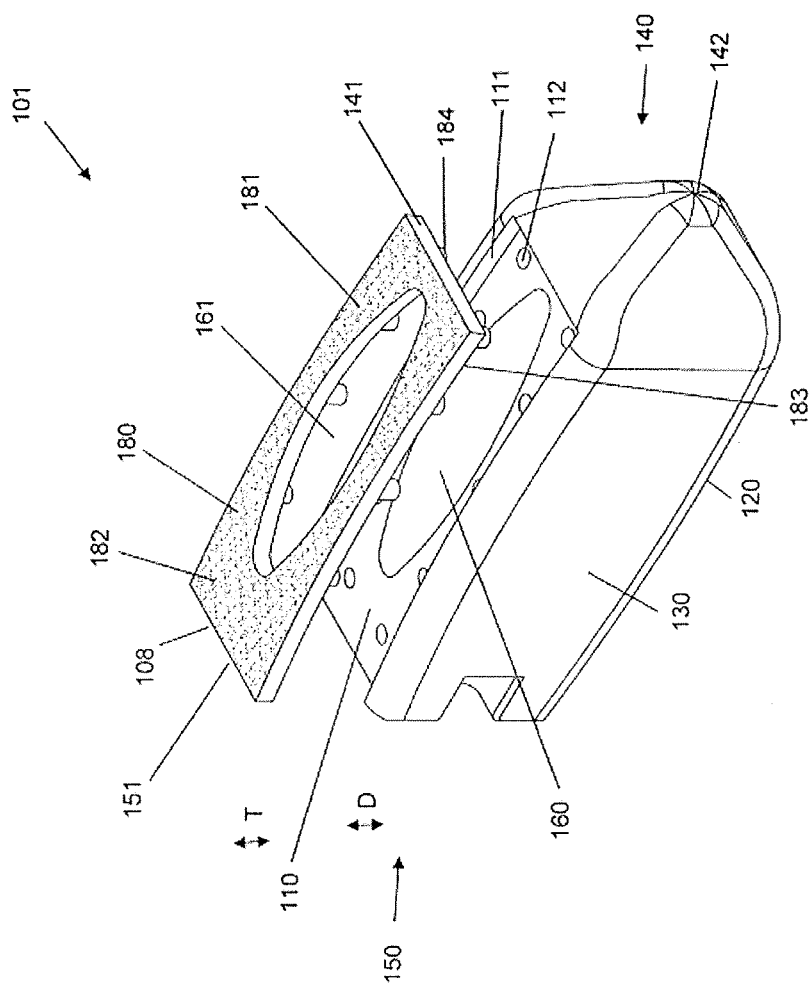
FIG. 15 shows an exploded view of a posterior implant with an integration plate.

As best shown in FIG. 14 and FIG. 15, the anterior portion 140, 140a may have a tapered nose 142, 142a to facilitate insertion of the implant 101.

The implant 1 may further include at least one transverse aperture 70 that extends the entire transverse length of the implant body. The transverse aperture 70 defines an interior surface or hollow cavity, which may be filled with bone growth-inducing materials. The at least one transverse aperture 70 may provide improved visibility of the implant 1 during surgical procedures to ensure proper implant placement and seating, and may also improve post-operative assessment of implant fusion. The transverse aperture 70 may be broken into two, separate sections by an intermediate wall.

Suitable shapes and dimensions for the transverse aperture 70 may be selected by one of ordinary skill in the art. In particular, all edges of the transverse aperture 70 may be rounded, smooth, or both. The intermediate wall may be made of the same material as the remainder of the body 2 of the implant 1 (e.g., plastic), or it may be made of another material (e.g., metal). The intermediate wall may offer one or more of several advantages, including reinforcement of the implant 1 and improved bone graft containment.

The implant 1 may be provided with a solid rear wall (not shown). The rear wall may extend the entire width of the implant body and nearly the entire height of the implant body. Thus, the rear wall can essentially close the anterior portion 40 of the implant 1. The rear wall may offer one or more of several advantages, including reinforcement of the implant 1 and improved bone graft containment. In the cervical application, it may be important to prevent bone graft material from entering the spinal canal.

The implant 1 may also have a lordotic angle to facilitate alignment. Depending on the implant 1 type, one lateral side 30 may be generally greater in height than the opposing lateral side 30 or the anterior portion 40 may be generally greater in height than the opposing posterior portion 50. Therefore, the implant 1 may better compensate for the generally less supportive bone found in certain regions of the vertebral endplate. Depending on the implant 1, as much as fifteen degrees or as much as seven degrees of lordosis (or more) may be built into the implant 1 to help restore cervical balance.

To enhance movement resistance and provide additional stability under spinal loads in the body, the implant 1, 101, 101a, 201, and 301 may comprise one or more anti-expulsion edges 8, 108, 108a, 208, and 308 that tend to "dig" into the end-plates slightly and help to resist expulsion. The anti-expulsion edges 8, 108, 108a, 208, and 308 may be present on the top surface 81 of the integration plate 82 affixed to the top surface 10, 110, 110a, 210, and 310; the bottom surface 20, 120, 120a, 220, and 320; or both surfaces of the implant 1, 101, 101a, 201, and 301. Alternatively, the anti-expulsion edges 8, 108, 108a, 208, and 308 may be present on the top surface 10, 110, 110a, 210, and 310; the bottom surface 20, 120, 120a, 220, and 320; or both surfaces of the body of the implant 1, 101, 101a, 201, and 301.

By way of example, FIG. 12 shows an anti-expulsion edge 8 on the top surface 81 of the integration plate 82 and the bottom surface 20 of the anterior face 40 of the implant 1. Each anti-expulsion edge 8 may protrude above the plane of the top surface 81 of the integration plate 82 and bottom surface 20, with the amount of protrusion increasing toward the anterior face 40 and the highest protrusion height P at the anterior-most edge of the top surface 81 of the integration plate 82 or bottom surface 20.

An anti-expulsion edge 8, 108, 108a, 208, and 308 may be oriented toward the anterior portion 40, 140, 140a, 240, and 340, or the posterior portion 50, 150, 150a, 250, and 350, or either of the opposing lateral sides 30, 130, 130a, 230, and 330. The orientation of the anti-expulsion edge 8, 108, 108a, 208, and 308 may depend on the intended orientation of the implant 1, 101, 101a, 201, and 301 when it has been implanted between vertebrae in the patient.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1, 101, 101a, 201, and 301 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant 1, 101, 101a, 201, and 301 is to be seated near the center of the vertebral endplate or the implant 1, 101, 101a, 201, and 301 is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant 1, 101, 101a, 201, and 301 into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a, 201, and 301 include smooth, rounded, and highly radiused posterior portions and lateral sides which may minimize extraneous bone removal for endplate preparation and reduce localized stress concentrations. Thus, interbody surgical implant 1, 101, 101a, 201, and 301 and methods of using it are particularly useful in preserving the natural arch of the vertebral endplate and minimizing the chance of implant subsidence.

Because the endplates are spared during the process of inserting the spinal implant 1, 101, 101a, 201, and 301, hoop stress of the inferior and superior endplates is maintained. Spared endplates allow the transfer of axial stress to the apophasis. Endplate flexion allows the bone graft placed in the interior of the spinal implant 1, 101, 101a, 201, and 301 to accept and share stress transmitted from the endplates. In addition, spared endplates minimize the concern that BMP might erode the cancellous bone.

Interbody spinal implant 1, 101, 101a, 201, and 301 is durable and can be impacted between the endplates with standard instrumentation. Therefore, certain embodiments of the invention may be used as the final distractor during implantation. In this manner, the disc space may be underdistracted (e.g., distracted to some height less than the height of the interbody spinal implant 1, 101, 101a, 201, and 301) to facilitate press-fit implantation. Further, certain embodiments of the current invention having a smooth and rounded posterior portion (and lateral sides) may facilitate easier insertion into the disc space. Still further, the surface roughened topography 80 may lessen the risk of excessive bone removal during distraction as compared to implants having teeth, ridges, or threads currently known in the art even in view of a press-fit surgical distraction method. Nonetheless, once implanted, the interbody surgical implant 1, 101, 101a, 201, and 301 may provide secure seating and prove difficult to remove. Thus, certain embodiments of the interbody spinal implant 1, 101, 101a, 201, and 301 may maintain a position between the vertebral endplates due, at least in part, to resultant annular tension attributable to press-fit surgical implantation and, post-operatively, improved osteointegration.

Surgical implants and methods according to embodiments of the invention tension the vertebral annulus via distraction. These embodiments may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, 101, 101a, 201, and 301, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101a, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants and the associated surgical technique have been designed to address at least the ten, separate challenges associated with the current generation of traditional anterior spinal fusion devices listed above in the Background section of this document.

After desired annulotomy and discectomy, embodiments of the invention first adequately distract the disc space by inserting (through impaction) and removing sequentially larger sizes of very smooth distractors, which have been size matched with the size of the available implant 1, 101, 101a, 201, and 301. Once adequate distraction is achieved, the surgeon prepares the end-plate with a rasp. There is no secondary instrumentation required to keep the disc space distracted while the implant 1, 101, 101a, 201, and 301 is inserted, as the implant 1, 101, 101a, 201, and 301 has sufficient mechanical strength that it is impacted into the disc space. In fact, the height of the implant 1, 101, 101a, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101a, 201, and 301 has adequate strength to allow impact, and the sides of the implant 1, 101, 101a, 201, and 301 may have smooth surfaces to allow for easy implantation and, specifically, to prevent binding of the implant 1, 101, 101a, 201, and 301 to soft tissues during implantation.

The invention encompasses a number of different implant 1, 101, 101a, 201, and 301 configurations, including a composite implant formed of top and optional bottom plates (components), for example, made out of titanium. The integration surfaces exposed to the vertebral body have a roughened surface topography 80 to allow for bony in-growth over time, and to provide resistance against expulsion. The top and bottom titanium plates may be assembled together with the implant body 2. The net result is a composite implant that has engineered stiffness for its clinical application. The axial load may be borne by the polymeric component of the construct.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101a, 201, and 301 designed according to certain embodiments allows the vertebral end-plate to deflect and allows healing of the bone graft into fusion.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. An interbody spinal implant, comprising:
   a body that is generally oval-shaped in transverse cross section, and comprises a top surface, a bottom surface, opposing lateral sides, opposing anterior and posterior portions, a substantially hollow center, and a single vertical aperture extending from the top surface to the bottom surface, having maximum width at its center, and, defining a transverse rim on the top surface and on the bottom surface, said transverse rim having a posterior thickness greater than an anterior thickness, and having a blunt and radiused portion along the top of each lateral side and the top of the posterior portion, wherein the portion of the transverse rim that is not blunt and radiused has a roughened surface topography including a repeating pattern in an organized arrangement adapted to grip bone and inhibit migration of the implant when the implant is placed between two vertebral endplates, but not including teeth, wherein the repeating pattern comprises at least three at least partially overlapping repeating patterns including a first repeating pattern, a second repeating pattern, and a third repeating pattern, provided that each of said repeating patterns does not contain a sharp point or undercut, and wherein the blunt and radiused portion does not include any roughened surface topography.

2. The spinal implant of claim 1, wherein the second repeating pattern radiates at a fixed distance from at least one point defined by the first repeating pattern.

3. The spinal implant of claim 2, wherein the third repeating pattern radiates at a fixed distance from at least one point defined by the first repeating pattern.

4. The spinal implant of claim 1, wherein each of the three repeating patterns comprises recesses having a slope of 30° or less relative to the top surface or the bottom surface.

5. The spinal implant of claim 1, wherein the first repeating pattern comprises recesses having a slope of 30° or less relative to the top surface or the bottom surface, the second repeating pattern comprises recesses having a slope of 25° or less relative to the top surface or the bottom surface, and the third repeating pattern comprises recesses having a slope of 20° or less relative to the top surface or the bottom surface.

6. The spinal implant of claim 1, wherein the three repeating patterns include: the first repeating pattern having a greatest depth, the second repeating pattern having an intermediate depth, and the third repeating pattern having a smallest depth.

7. The spinal implant of claim 6, wherein the three repeating patterns include: the first repeating pattern having a spacing S1, the second repeating pattern having a spacing S2, and the third repeating pattern having a spacing S3, wherein the spacing S1<spacing S3<spacing S2.

8. The spinal implant of claim 1, wherein each of the three repeating patterns comprises an array of dots, spheres, semi-spheres, cubes, polyhedral pyramids, or amorphous shapes.

9. The spinal implant of claim 8, wherein each of the three repeating patterns comprises spheres or semi-spheres.

10. The spinal implant of claim 9, wherein each of the three repeating patterns comprises spheres or semi-spheres having varying diameters.

11. The spinal implant of claim 1, wherein each of the three repeating patterns comprise features having diameters, depths, and spacings which are sequentially sized and positioned to preserve an amount of the features and patterns from the previous pattern.

12. The spinal implant of claim 1, wherein the roughened surface topography includes the three repeating patterns of smooth shapes oriented in opposition to the biologic forces on the implant and to the insertion direction.

13. The spinal implant of claim 1 wherein the implant is adapted to (a) not damage the vertebral endplates and (b) to disperse the load from the vertebral endplates.

14. The spinal implant of claim 1, wherein the implant has a sharp edge at the junction of the top surface and the anterior portion and at the junction of the bottom surface and the anterior portion.

15. The spinal implant of claim 1, wherein the first repeating pattern is arranged in a first array of columns and rows oriented along an x-axis and a y-axis.

16. The spinal implant of claim 15, wherein the second repeating pattern is arranged in a second array of columns and rows oriented along the x-axis and y-axis.

17. The spinal implant of claim 16, wherein the third repeating pattern is arranged in a third array of columns and rows oriented along the x-axis and y-axis.

18. The spinal implant of claim 17, wherein each of the first, second, and third repeating patterns surround the single vertical aperture.

* * * * *